United States Patent [19]
Elmer et al.

[11] Patent Number: 5,850,023
[45] Date of Patent: Dec. 15, 1998

[54] MODIFIED PLANT VIRAL REPLICASE GENES

[75] Inventors: James Scott Elmer, East Raleigh, N.C.; Daniel Nathans, Baltimore, Md.; Stephen Gary Rogers, St. Louis, Mo.

[73] Assignee: Monsanto Company, St. Louis, Mo.

[21] Appl. No.: 967,999

[22] Filed: Nov. 12, 1997

Related U.S. Application Data

[63] Continuation of Ser. No. 563,227, Nov. 27, 1995, abandoned, which is a continuation of Ser. No. 259,733, Jun. 13, 1994, abandoned, which is a continuation of Ser. No. 982,799, Nov. 30, 1992, abandoned.

[51] Int. Cl.[6] .............................. A01H 1/04; C07H 21/04; C12N 15/00
[52] U.S. Cl. .................................. 800/205; 800/DIG. 43; 800/DIG. 44; 435/172.3; 435/320.1; 536/23.72; 935/10
[58] Field of Search .............................. 435/172.1, 172.3, 435/320.1; 800/205, DIG. 43, DIG. 44; 536/23.1, 23.2, 23.72, 24.1; 935/10, 64

[56] References Cited

U.S. PATENT DOCUMENTS

| | | | |
|---|---|---|---|
| 5,580,716 | 12/1996 | Johnston et al. ............................. | 435/5 |
| 5,596,132 | 1/1997 | Zaitlin et al. ............................ | 800/205 |
| 5,633,449 | 5/1997 | Zaitlin et al. ............................ | 800/205 |

FOREIGN PATENT DOCUMENTS

WO 91/13542 9/1991 WIPO .............................. A01H 5/00

OTHER PUBLICATIONS

W Möller et al (1985) FEBS Letters 186:1–7.
JM Farber et al (1987) J. Virol. 618: 436–445.
L Hanley–Bowdoin (1990) Proc Natl Acad Sci USA 87: 1446–1450.
S Bagga et al (1992) Plant Molecular Biology 19:951–958.
JM Farber et al (1987) J Virol. 61:436–445.
L Hanley–Bowdoin (1990) Proc Natl Acad Sci, USA 87: 1446–1450.
Zhu, *Journal of Virology*, 63: 4777 (1989).
Rochester, *Virology*, 178: 001 (1990).
USDA grant application (Dec. 1991).
Anderson, et al. (1992) *Proc. Natl. Acad. Sci. USA* 89:8759–8763.
Braun, Carl J. and Hemenway, Cynthia L., (1992) *The Plant Cell* 4:735–744.
Carr, Peter and Zaitlin, Milton (1993) Seminars in Virology 4:339–347.
Golemboski, et al. (1990) *Proc. Natl. Sci. USA* 87:6311–6315.
Hodgman (1988) *Nature* 333:22–23.
Inokuchi, et al. J. Virology 61(12):3946–49, 1987.
Ishikawa, et al. (1986) *Nucleic Acids Res.* 14:8291–8305.
MacFarlane, et al. (1992) *Proc. Natl. Acad. Sci. USA* 89:5829–5833.
Taschner, et al. (1991) *Virology* 181:445–450.
Rao et al. (1991) Virology 180, 16–22.
van Dun, et al., (1988) *Virology* 163:572–578.

*Primary Examiner*—Bruce R. Campell
*Attorney, Agent, or Firm*—Dennis R. Hoerner, Jr.; Arnold, White & Durkee

[57] ABSTRACT

DNA sequences encoding plant viral proteins which contain modifications of the amino acid sequence -Gly1-Xaa1-Xaa2-Xaa3-Xaa4-Gly2-Lys- are disclosed. These modified proteins confer viral resistance when expressed in transformed plants. A method for providing resistance to infection by a geminivirus in a susceptible plant are disclosed. Plants expressing the modified genes which are resistant to viral infection are also disclosed.

15 Claims, 12 Drawing Sheets

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Gly Xaa Xaa Xaa Xaa Gly Lys
   1               5

( 2 ) INFORMATION FOR SEQ ID NO:2:

( i ) SEQUENCE CHARACTERISTICS:
      ( A ) LENGTH: 27 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:2:

Ile Pro Lys Lys Arg Tyr Trp Leu Phe Lys Gly Pro Ile Asp Ser Gly
   1               5                   10                  15
   Lys Thr Thr Leu Ala Ala Ala Leu Leu Glu Leu
                   20                  25

( 2 ) INFORMATION FOR SEQ ID NO:3:

( i ) SEQUENCE CHARACTERISTICS:
      ( A ) LENGTH: 27 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

Val Pro Lys Lys Arg Asn Val Leu Phe Arg Gly Pro Val Asn Ser Gly
   1               5                   10                  15
   Lys Thr Ser Leu Ala Ala Ala Ile Met Asn Leu
                   20                  25

( 2 ) INFORMATION FOR SEQ ID NO:4:

( i ) SEQUENCE CHARACTERISTICS:
      ( A ) LENGTH: 27 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

Pro Glu Arg Pro Ile Ser Ile Ile Val Glu Gly Asp Ser Arg Thr Gly
   1               5                   10                  15
   Lys Thr Met Trp Ala Arg Ala Leu Gly Pro His
                   20                  25

( 2 ) INFORMATION FOR SEQ ID NO:5:

( i ) SEQUENCE CHARACTERISTICS:

( A ) LENGTH: 27 amino acids
( B ) TYPE: amino acid
( D ) TOPOLOGY: linear ( i i ) MOLECULE TYPE: peptide ( x i ) SEQUENCE DESCRIPTION: SEQ ID NO:5:

Pro Glu Arg Pro Ile Ser Ile Ile Val Glu Gly Asp Ser Arg Thr Gly
1               5                   10                  15
Lys Thr Met Trp Ala Arg Ala Leu Gly Pro His
            20                  25

( 2 ) INFORMATION FOR SEQ ID NO:6:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( x i ) SEQUENCE DESCRIPTION: SEQ ID NO:6:

Pro Leu Arg Tyr Asn Ser Ile Ile Val Glu Gly Asp Ser Arg Thr Gly
1               5                   10                  15
Lys Thr Met Trp Ala Arg Ser Leu Gly Ala His
            20                  25

( 2 ) INFORMATION FOR SEQ ID NO:7:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( x i ) SEQUENCE DESCRIPTION: SEQ ID NO:7:

Pro Leu Arg Tyr Asn Ser Ile Ile Val Glu Gly Asp Ser Arg Thr Gly
1               5                   10                  15
Lys Thr Met Trp Ala Arg Ser Leu Gly Ala His
            20                  25

( 2 ) INFORMATION FOR SEQ ID NO:8:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( x i ) SEQUENCE DESCRIPTION: SEQ ID NO:8:

Gly Val Arg Arg Arg Ser Leu Tyr Ile Cys Gly Pro Thr Arg Thr Gly
1               5                   10                  15
Lys Thr Ser Trp Ala Arg Ser Leu Gly Thr His
            20                  25

( 2 ) INFORMATION FOR SEQ ID NO:9:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( x i ) SEQUENCE DESCRIPTION: SEQ ID NO:9:

```
Pro  Gly  Arg  His  Lys  Ser  Ile  Tyr  Ile  Cys  Gly  Pro  Thr  Arg  Thr  Gly
1                   5                        10                       15

Lys  Thr  Ser  Trp  Ala  Arg  Ser  Leu  Gly  Thr  His
                    20                   25
```

(2) INFORMATION FOR SEQ ID NO:10:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:10:

```
Arg  Ser  Arg  Lys  Gln  Ser  Leu  Tyr  Ile  Val  Gly  Pro  Thr  Arg  Thr  Gly
1                   5                        10                       15

Lys  Ser  Thr  Trp  Ala  Arg  Ser  Leu  Gly  Val  His
                    20                   25
```

(2) INFORMATION FOR SEQ ID NO:11:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:11:

```
Phe  Lys  Ser  Phe  Val  Asn  Leu  Asn  Tyr  Lys  Gly  Asp  Ser  Lys  Leu  Gly
1                   5                        10                       15

Arg  Asn  Ile  Arg  Trp  Gln  Ala  Trp  Leu  Ser
                    20                   25
```

(2) INFORMATION FOR SEQ ID NO:12:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:12:

```
Ala  Val  Gly  Ala  Leu  Tyr  Ser  Gly  Lys  Lys
1                   5                        10
```

(2) INFORMATION FOR SEQ ID NO:13:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:13:

```
Ala  Met  Gly  Ala  Leu  Tyr  Lys  Gly  Lys  Lys
1                   5                        10
```

(2) INFORMATION FOR SEQ ID NO:14:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO:14:

Ala Val Gly Ala Leu Tyr Ser Gly Lys Lys
1               5                   10

(2) INFORMATION FOR SEQ ID NO:15:

(i) SEQUENCE CHARACTERISTICS:
       (A) LENGTH: 10 amino acids
       (B) TYPE: amino acid
       (D) TOPOLOGY: linear (i i) MOLECULE TYPE: peptide (x i) SEQUENCE DESCRIPTION: SEQ ID NO:15:

Ala Val Gly Ala Ser Tyr Gly Cys Lys Lys
1               5                   10

(2) INFORMATION FOR SEQ ID NO:16:

(i) SEQUENCE CHARACTERISTICS:
       (A) LENGTH: 10 amino acids
       (B) TYPE: amino acid
       (D) TOPOLOGY: linear (i i) MOLECULE TYPE: peptide (x i) SEQUENCE DESCRIPTION: SEQ ID NO:16:

Gln Ser Gly Asn Glu Asp Ala Gly Lys Gln
1               5                   10

(2) INFORMATION FOR SEQ ID NO:17:

(i) SEQUENCE CHARACTERISTICS:
       (A) LENGTH: 10 amino acids
       (B) TYPE: amino acid
       (D) TOPOLOGY: linear (i i) MOLECULE TYPE: peptide (x i) SEQUENCE DESCRIPTION: SEQ ID NO:17:

Lys Arg Gly Arg Arg Gly Gly Lys Asn Lys
1               5                   10

(2) INFORMATION FOR SEQ ID NO:18:

(i) SEQUENCE CHARACTERISTICS:
       (A) LENGTH: 8 amino acids
       (B) TYPE: amino acid
       (D) TOPOLOGY: linear (i i) MOLECULE TYPE: peptide (x i) SEQUENCE DESCRIPTION: SEQ ID NO:18:

Gly Gly Pro Gly Thr Gly Lys Ser
1               5

(2) INFORMATION FOR SEQ ID NO:19:

(i) SEQUENCE CHARACTERISTICS:
       (A) LENGTH: 8 amino acids
       (B) TYPE: amino acid
       (D) TOPOLOGY: linear (i i) MOLECULE TYPE: peptide (x i) SEQUENCE DESCRIPTION: SEQ ID NO:19:

Gly Ala Gly Gly Ser Gly Lys Ser

```
            1               5
```

(2) INFORMATION FOR SEQ ID NO:20:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:20:

```
Gly Glu Tyr Leu Thr Gly Lys Ile
1               5
```

(2) INFORMATION FOR SEQ ID NO:21:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:21:

```
Gly Val Pro Gly Cys Gly Lys Ile
1               5
```

(2) INFORMATION FOR SEQ ID NO:22:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:22:

```
Val Asp Gly Val Ala Gly Cys Gly Lys Thr
1               5                   10
```

(2) INFORMATION FOR SEQ ID NO:23:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:23:

```
Val Asp Gly Val Ala Gly Cys Gly Lys Thr
1               5                   10
```

(2) INFORMATION FOR SEQ ID NO:24:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:24:

```
Val Asp Gly Val Ala Gly Cys Gly Lys Thr
1               5                   10
```

(2) INFORMATION FOR SEQ ID NO:25:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:25:

Val Asp Gly Val Pro Gly Cys Gly Lys Thr
1               5                   10

( 2 ) INFORMATION FOR SEQ ID NO:26:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:26:

Gly Xaa Xaa Xaa Xaa Ala Leu Glu Lys
1               5

( 2 ) INFORMATION FOR SEQ ID NO:27:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:27:

Gly Xaa Thr Leu Glu Lys
1               5

( 2 ) INFORMATION FOR SEQ ID NO:28:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:28:

GTAGTAAGCC AGATCTTAAT TACAAAACAT ATGCCATCG    39

( 2 ) INFORMATION FOR SEQ ID NO:29:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:29:

ATAGTCGGAC GGCTCTAGAG AAGACTATGT    30

( 2 ) INFORMATION FOR SEQ ID NO:30:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear -continued ( i i ) MOLECULE TYPE: DNA (synthetic)

( x i ) SEQUENCE DESCRIPTION: SEQ ID NO:30:

TCGAGGGCGA TACTCTAGAG AAGACTATGT 30

MODIFIED PLANT VIRAL REPLICASE GENES

This application is a continuation of application Ser. No. 08/563,227, filed Nov. 27, 1995, abandoned, which is a continuation of application Ser. No. 08/259,733, filed Jun. 13, 1994, abandoned, which is a continuation of application Ser. No. 07/982,799, filed Nov. 30, 1992, abandoned.

FIELD OF THE INVENTION

The present invention is related to the genetic engineering of plants. In particular the present invention relates to genetically modified plants which are resistant to viruses.

BACKGROUND OF THE INVENTION

A significant problem in agriculture today is the infection of crop species by plant viruses. Many agriculturally important crops are susceptible to infection by plant viruses. These viruses can seriously damage a crop and drastically reduce its economic value to the grower by decreasing yields and reducing the quality of many crop products. Many attempts have been made to eliminate or control viral infection of crops, but the problem still persists. This has ultimately led to a higher cost for the consumer. Attempts to control or prevent infection of a crop by a plant virus have been made, yet viral pathogens continue to be a significant problem in agriculture.

Scientists have recently developed means to produce virus resistant plants using genetic engineering techniques. Such an approach is advantageous in that the means for providing the protection is incorporated in the plant itself and can be passed on to its progeny. A host plant is resistant if it possesses the ability to suppress or retard the multiplication of a virus, or the development of pathogenic symptoms. "Resistant" is the opposite of "susceptible", and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

Genes which interfere with the process of virus replication and/or infection may be expressed in transgenic plants to protect against infection. It has previously been shown that expression of a plant virus capsid protein, which is termed the coat protein, in a plant can confer resistance to the homologous virus and to related viruses (Abel et al. 1986; Turner et al. 1987: Cuozzo et al. 1988; Hemenway et al. 1988; Stark and Beachy 1989; Lawson et al. 1990; Kaniewski et al. 1990). In these studies, resistance to virus disease is defined as either reduced incidence of infection, delayed symptom development, reduced virus replication or viral antigen levels, or slower to no systemic virus movement. Expression of the virus coat protein in these transgenic plants is responsible for the observed effects in the reduction of virus disease by an as yet undetermined mechanism (Abel et al. 1986; van Dun et al. 1988). This type of protection against viral infection is termed coat protein-mediated protection.

Even though coat protein-mediated viral resistance has proven to be useful in a variety of situations, it may not always be the most effective or the most desirable means for providing viral resistance. In such instances, it would be advantageous to have other methods for conferring viral resistance to plants.

A fragment of the putative replicase gene from tobacco mosaic virus (TMV) recently has been found to provide resistance against TMV when expressed in tobacco plants (Golemboski et al. 1990). In TMV, two proteins, the 183 kDa and 126 kDa proteins, have been speculated to be replicase components, as the expression of both proteins are necessary for normal multiplication in tobacco plants (Ishikawa et al. 1986). The 183 kDa protein is a read-through product of the 126 kDa sequence. The 126 kDa protein contains the NTP binding motif. The 183 kDa protein contains both the NTP and GDD motifs. More specifically, the 54 kDa readthrough portion of the 183 kDa protein is the portion that contains the GDD motif. Golemboski et al. (1990) found that transgenic tobacco plants expressing the 54 kDa read-through portion were protected against infection by TMV. They did not, however, observe protection in transgenic plants expressing the larger 126 kDa protein. Moreover, they did not report any protection data from experiments in which the plants expressed the 183 kDa protein.

Others have conducted protection experiments with transgenic plants expressing components of non-structural viral proteins. For example, van Dun et al. (1988) analyzed protection in tobacco plants expressing either of two genes encoding proteins involved in the replication of alfalfa mosaic virus (AlMV). These plants were transformed with RNAs 1 or 2 of AlMV, which encode proteins P1 and P2, respectively. The polypeptides encoded by these RNAs have amino acid homologies to other viral replicases, and both RNAs are known to be essential for replication. In contrast to the PVY ORF1, the NTP and GDD binding motifs for AlMV are encoded on different RNAs and consequently different proteins. The replicase protein here also contains the GDD domain found in many proteins capable of replicating nucleic acids (Hodgman, 1981). The GDD domain contains a glycine amino acid residue (G) followed by two aspartate amino acid residues (D). GDD domains are often found in replicase proteins and are believed to be involved in catalytic function. In particular, P1 on RNA1 has homology to the NTP binding motif and P2 on RNA2 has homology to the GDD motif. Plants expressing either RNA1 or RNA2 were not protected against infection by AlMV. In addition, plants expressing both RNAs 1 and 2 were likewise not protected against infection by AlMV (Taschner et al. 1991).

Buck et al. (PCT publication WO 92/03539) have described the use of various techniques to prevent the expression or function of a cucumber mosaic viral replicase in order to provide viral resistance in plants, including the expression of a fragment of the replicase gene in order to provide this viral resistance. The techniques employed or disclosed in this publication to accomplish this included: 1) antisense technology (wherein a complementary RNA to that coding for the full length replicase was expressed); 2) expression of a gene coding for an antibody specific for one of the three components of the replicase (viral encoded polypeptides P1a and P2a, and polypeptide P50 from tobacco); 3) a truncated form or fragment of the replicase; and 4) use of a ribozyme specific for the RNA coding for one of the components of the replicase.

Another potential source of genes which interfere with viral replication are mutated genes which show trans-dominant interference. These are mutants which express proteins that have not only lost the ability to function normally themselves, but also interfere with the function of the non-mutated proteins they are derived from.

Several mutations in the SV40-TAg which act in a trans-dominant manner to interfere with normal TAg function in regard to viral replication have been reported (Farber, 1987; Zhu, 1989). The large tumor antigen (TAg) from simian virus 40 (SV40) is a large (95 kd), multi-functional protein. SV40-TAg plays a vital role in the oncogenic transformation of mammalian cells and in SV40 viral DNA replication. The TAg is known to bind to the SV40 viral DNA origin of replication and act as a helicase (Stahl, 1986; Kelly, 1988). The TAg has also been shown to bind ATP and operate as an ATPase (Bradley, 1984; Clark, 1983). The helicase activity of the TAg is dependent upon this ATPase activity (Stahl, 1986). In addition, the presence of ATP has been shown to enhance the binding of TAg to the viral origin of replication (Borowiec, 1988).

The ATP binding site of the SV40-TAg has been characterized extensively, mainly through analysis of mutants and by comparison with other proteins known to bind ATP. Through analysis of TAg mutants, regions of the protein have been identified which are necessary for ATP catalytic activity/binding or, more generally, viral DNA replication (Auborn, 1989; Loeber, 1989). Some of these regions share homology with other proteins which bind ATP (Bradley, 1987; Serrano, 1989). Based on this information, computer models which predict the 3-dimensional structure of the ATP binding site for several proteins (including TAg) have been generated (Bradley, 1987; Serrano, 1989). These models include as one common feature the presence of a glycine rich loop predicted to catalyze the transfer of phosphate during ATP hydolysis. In some ATP binding proteins, including SV40-TAg, this glycine rich loop is present as a -Gly1-Xaa1-Xaa2-Xaa3-Xaa4-Gly2-Lys- domain (SEQ ID NO. 1). Alternatively, in this domain, the -Lys- may be replaced by -Arg-. Mutations which alter this sequence in the SV40-TAg have been shown to either directly affect ATPase activity (Clark, 1983) or affect the ability of TAg to replicate SV40 DNA, a function associated with ATP binding/catalysis (Manos, 1985; Farber, 1987). These are examples of mutations which generate the trans-dominant interference effect.

Despite the functional and physical differences between the SV40-TAg and plant viral proteins involved in viral replication, the present invention demonstrates a similar trans-dominant effect that results from mutations in the amino acid sequence -Gly1-Xaa1-Xaa2-Xaa3-Xaa4-Gly2-Lys- (SEQ ID NO. 1). It would be unexpected that modifications in the plant viral proteins would function in a similar manner to those modifications in the SV40-TAg, an animal viral protein. This invention makes a significant contribution to the art by providing an alternative method for conferring viral resistance to plants, which employs a class of mutated plant viral genes expressed in plants.

SUMMARY OF THE INVENTION

It is an object of the present invention to provide an isolated DNA molecule derived from a plant virus which comprises a modified structural gene encoding a modified protein normally required for the replication of a plant virus which protein normally comprises an amino acid domain having the sequence -Gly1-Xaa1-Xaa2-Xaa3-Xaa4-Gly2-Lys- (SEQ ID NO. 1) but having a modification of said nucleic acid sequence which results in a modification of said amino acid domain which produces resistance to said virus in transgenic plants expressing said modified protein.

It is another object of this invention to provide a DNA molecule which comprises:

(a) a promoter region which functions in plant cells to cause the production of an RNA sequence;
which is operably linked to (b) a structural gene encoding a protein which has the following characteristics:
   (i) said protein is normally required for the replication of a plant virus;
   (ii) said protein contains a modification within the amino acid domain -Gly1-Xaa1-Xaa2-Xaa3-Xaa4-Gly2-Lys- (SEQ ID NO. 1);
which is operably linked to (c) a 3' non-translated DNA sequence which functions in plant cells to cause the termination of transcription and the addition of polyadenylated ribonucleotides to the 3' end of the transcribed mRNA sequence.

It is yet another object of the present invention to provide a method for providing resistance to infection by a geminivirus in a susceptible plant which comprises:

(a) transforming susceptible plant cells with a DNA molecule which comprises:
   (i) a promoter region which functions in plant cells to cause the production of an RNA sequence;
which is operably linked to
   (ii) a structural gene encoding a protein which has the following characteristics:
      (a') said protein is normally required for the replication of said geminivirus;
      (b') said protein contains a modification within the amino acid domain -Gly1-Xaa1-Xaa2-Xaa3-Xaa4-Gly2-Lys- (SEQ ID NO. 1);
which is operably linked to
   (iii) a 3' non-translated DNA sequence which functions in plant cells to cause the termination of transcription and the addition of polyadenylated ribonucleotides to the 3' end of the transcribed mRNA sequence;
wherein said protein is derived from a geminivirus which is capable of infecting said plant;

(b) selecting said plant cells which have been transformed;

(c) regenerating said plant cells to provide a differentiated plant; and (d) selecting a transformed plant which expresses said structural gene at a level sufficient to render the plant resistant to infection by said geminivirus.

Yet another object of the present invention is to provide a virus resistant transformed plant which contains a gene derived from a plant virus which comprises a modified structural gene encoding a modified protein normally required for the replication of a plant virus which protein normally comprises an amino acid domain having the sequence -Gly1-Xaa1-Xaa2-Xaa3-Xaa4-Gly2-Lys- but having a modification of said nucleic acid sequence which results in a modification of said amino acid domain which produces resistance to said virus in transgenic plants expressing said modified protein.

Other objects, aspects, and advantages of the present invention will be apparent to those skilled in the art from the following description, Example, and claims.

DETAILED DESCRIPTION OF THE INVENTION

Figure 1:
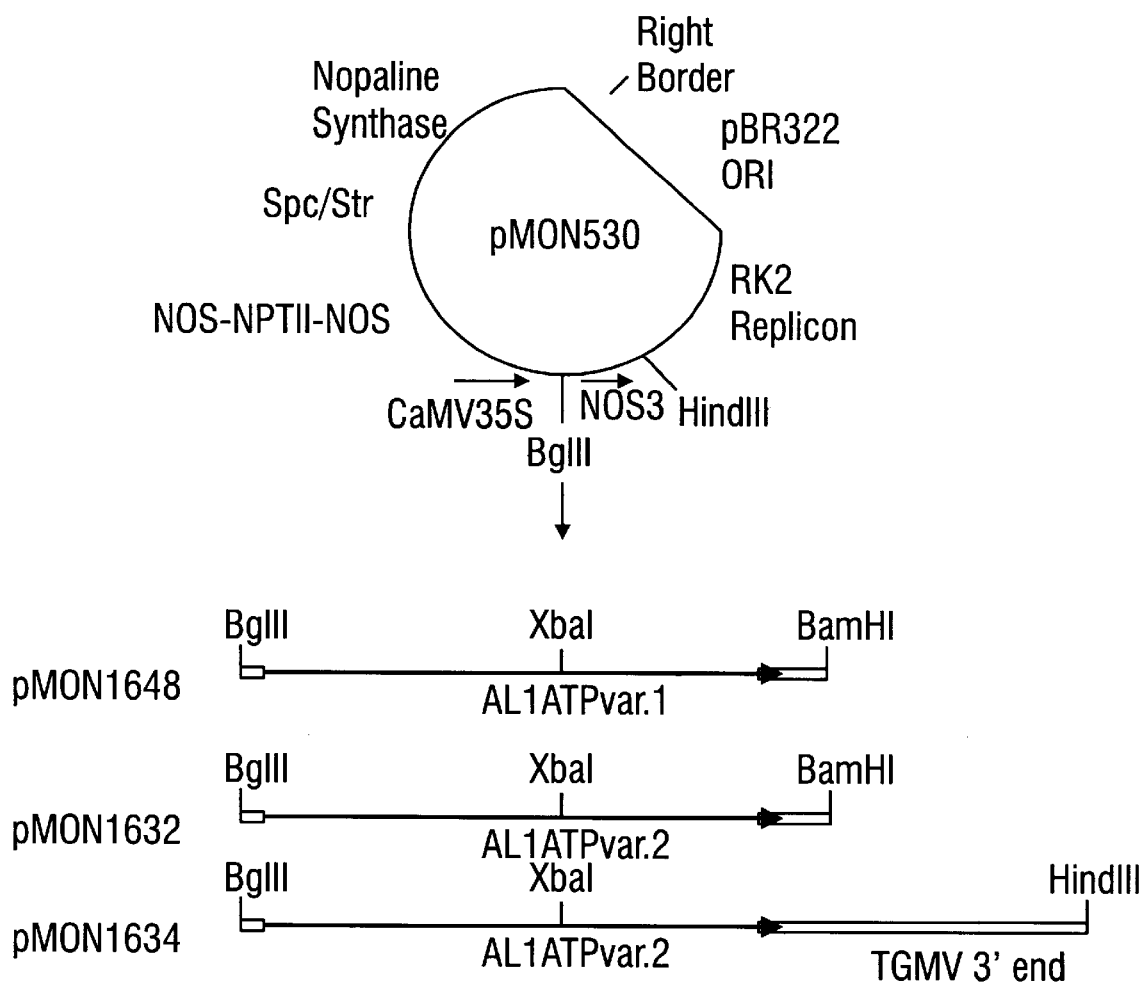
FIG. 1 illustrates pMON 530 and derivatives. Black and white lines represent coding and noncoding sequences, respectively. The designated Xba I sites mark the position of the modifications made to the AL1 coding sequence.
Figure 2:
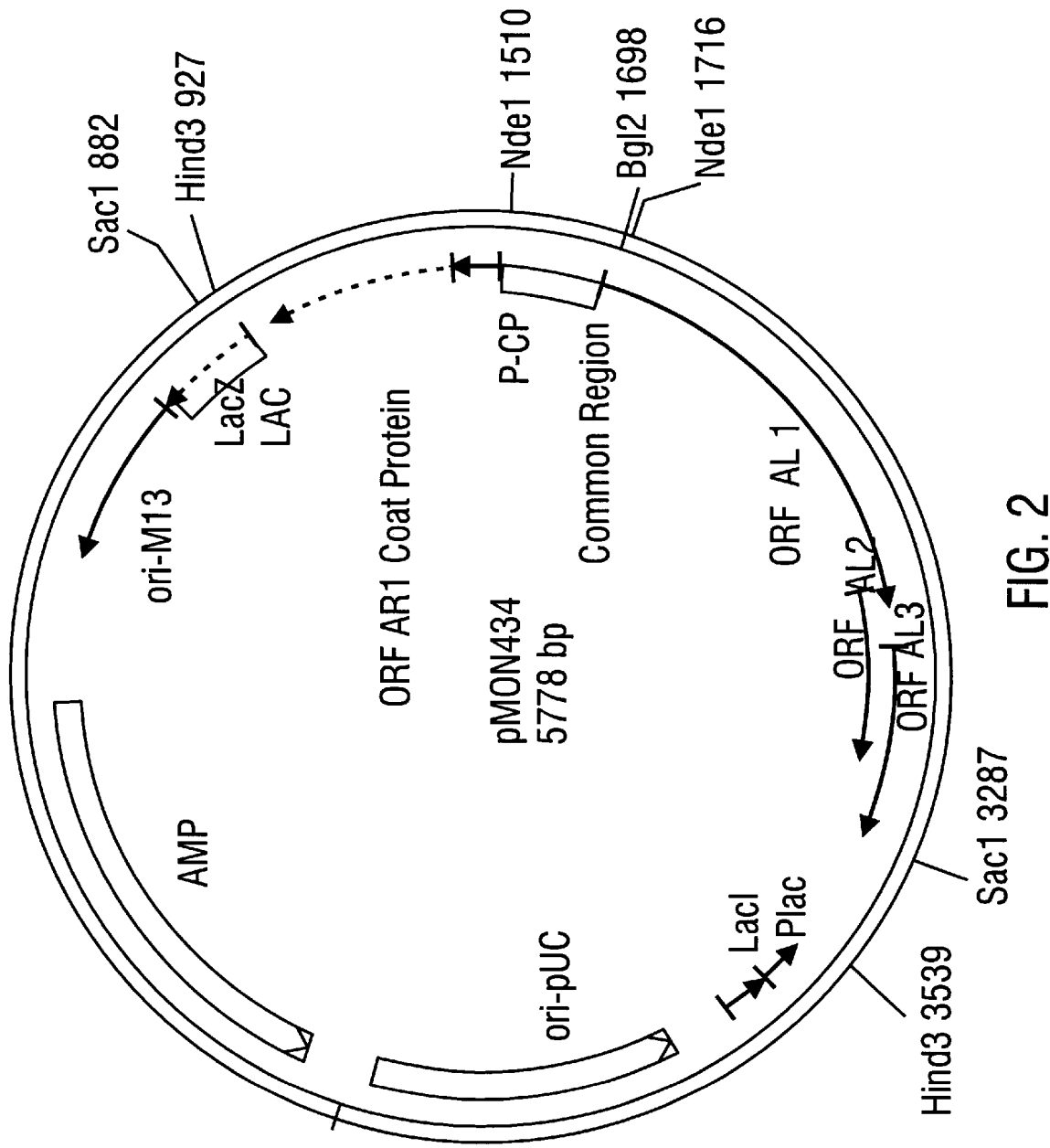
FIG. 2 illustrates pMON434.
Figure 3:
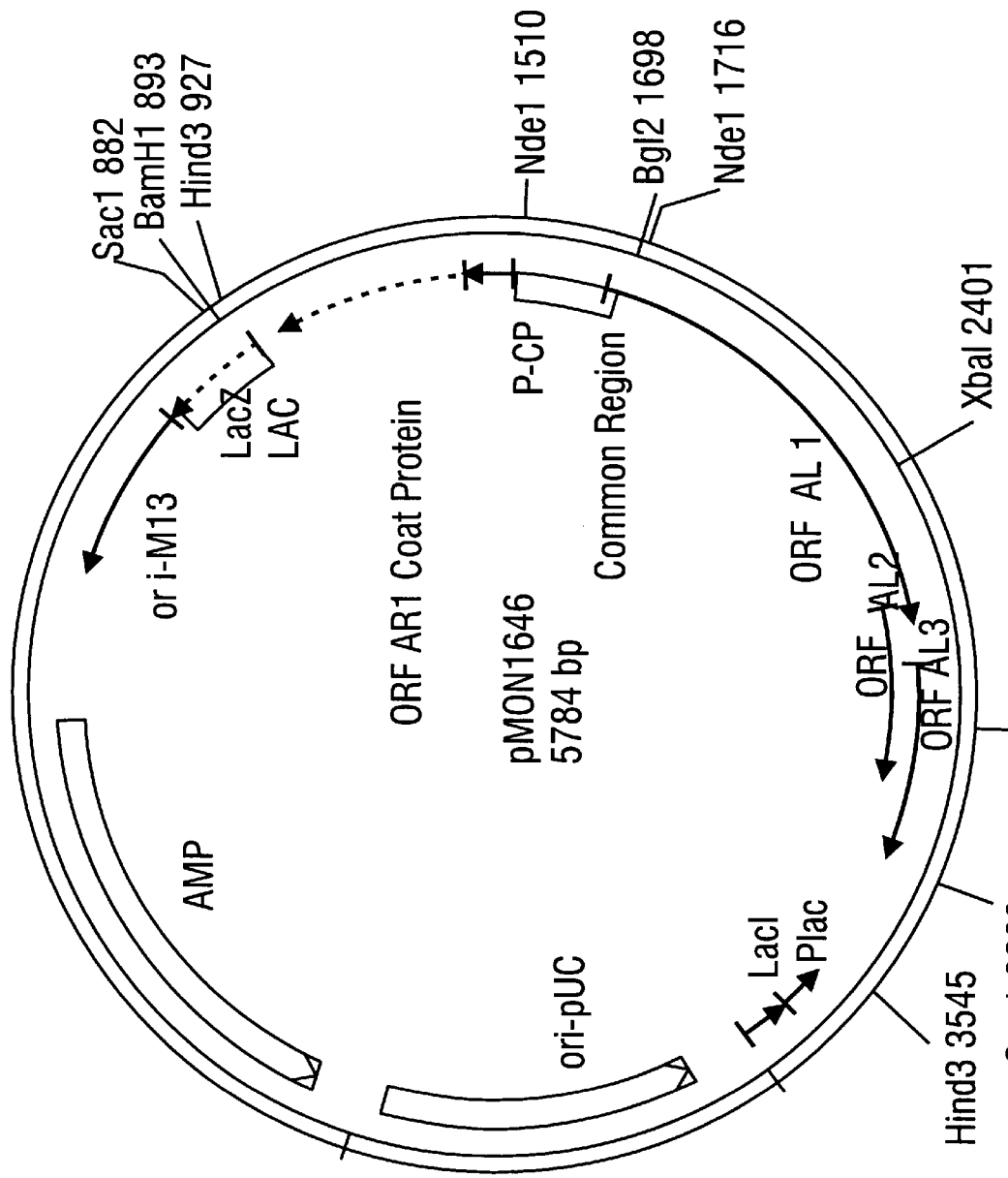
FIG. 3 illustrates pMON1646.
Figure 4:
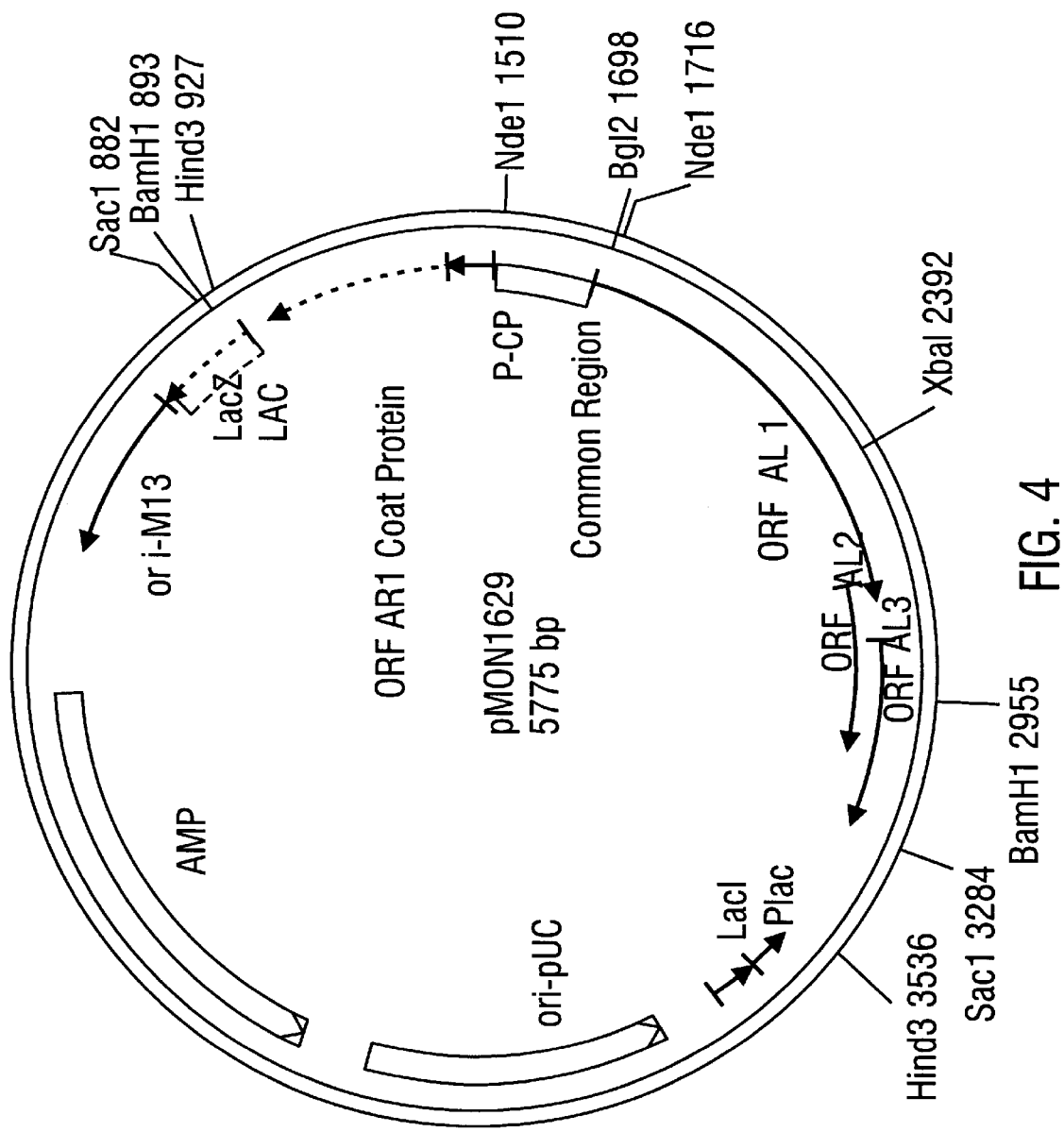
FIG. 4 illustrates pMON1629.

The viral resistance conferred to plants of the present invention is provided by the expression in planta of a DNA molecule derived from a plant virus comprising nucleotides which code for a protein normally required for the replication of the viral genome. Examples include proteins which demonstrate replicase activity, RNA polymerase activity, reverse transcriptase activity, helicase activity, ATP hydrolysis activity, GTP hydrolysis activity, primase activity, nucleic acid binding activity, nicking activity, and combinations thereof. This protein would also contain the amino acid sequence -Gly1-Xaa1-Xaa2-Xaa3-Xaa4-Gly2-Lys- (SEQ ID NO. 1 ) which has been modified in some manner. Alternatively, the -Lys- may instead be -Arg-. X would typically be any amino acid. Modifications to the DNA are made within the coding region for the -Gly1-Xaa1-Xaa2-Xaa3-Xaa4-Gly2-Lys- (SEQ ID NO. 1) amino acid sequence and result in a change in the amino acid sequence. These modifications may include deletions, additions, substitutions, and combinations thereof. Genes identified by the criteria above may be modified to produce embodiments of the present invention by mutagenesis procedures familiar to those skilled in the art.

Suitable plant viruses from which this DNA molecule may be isolated are viruses from the geminivirus group, which include but are not limited to abutilon mosaic, beet curly top, bean golden mosaic, cassava latent, chloris striate mosaic, digitaria streak, Florida tomato, maize streak, mung bean yellow mosaic, potato yellow mosaic, squash leaf curl, tomato golden mosaic, tomato yellow leaf curl, and wheat dwarf virus. Geminiviruses are known to infect *Leguminosae, Malvaceae, Solanaceae, Gramineae, Chenopodiaceae*, and *Compositae* families. Tomato Golden Mosaic Virus is known to infect all species of the *Solanaceae* family. For the sake of clarity and brevity of explanation, the following description of the particular embodiments of this invention will be exemplified by the use of tomato golden mosaic virus (TGMV).

Table 1 provides a list of various viruses and their respective consensus amino acid sequences of the viral proteins involved in replication. (It is to be understood that the N-terminus is to the left of the amino acid sequence as represented in the Table and in other places throughout the specification, and the C-terminus is to the right of the sequence as represented, as is common practice among those of skill in the art. The consensus sequence of Table 1 is centered and bolded for ease of representation.)

TABLE 1

| Consensus Amino Acid Sequence Among Viral Replication Proteins | | | | |
|---|---|---|---|---|
| SV40 large T-antigen | IPKKRYWLFK | GPIDSGK | TTLAAALLEL | SEQ ID NO.2 |
| Polyomavirus T-antigen | VPKKRNVLFR | GPVNSGK | TSLAAAIMNL | SEQ ID NO.3 |
| TGMV AL1 | PERPISIIIE | GDSRTGK | TMWARSLGPH | SEQ ID NO.4 |
| BGMV AL1 | PERPISIIVE | GDSRTGK | TMWARALGPH | SEQ ID NO.5 |
| ACMV AL1 | PWRPNSIVIE | GDSRTGK | TIWARSLGPH | SEQ ID NO.6 |
| BCTV AL1 | PLRYNSIIVE | GDSRTGK | TMWARSLGAH | SEQ ID NO.7 |
| CSMV AL1 | GVRRRSLYIC | GPTRTGK | TSWARSLGTH | SEQ ID NO.8 |
| WDV AL1 | PGRHKSIYIC | GPTRTGK | TSWARSLGTH | SEQ ID NO.9 |
| MSV AL1 | RSRKQSLYIV | GPTRTGK | STWARSLGVH | SEQ ID NO.10 |
| CaMV reverse transcriptase | FKSFVNLNYK | GDSKLGR | NIRWQAWLS | SEQ ID NO.11 |
| PP-NAT | AV | GALYSGK | K | SEQ ID NO.12 |
| TEV | AM | GALYKGK | K | SEQ ID NO.13 |
| TVMV | AV | GALYSGK | K | SEQ ID NO.14 |
| PVY-N | AV | GASYGC | KK | SEQ ID NO.15 |
| JGMV | QS | GNEDAGK | Q | SEQ ID NO.16 |
| PLRV | KR | GRRGGKN | K | SEQ ID NO.17 |
| BNYVV | | GGPGTGK | S | SEQ ID NO.18 |
| PVX-1 | | GAGGSGK | S | SEQ ID NO.19 |
| PVX-2 | | GEYLTGK | I | SEQ ID NO.20 |
| TMV | | GVPGCGK | I | SEQ ID NO.21 |
| AlMV | | VDGVAGCGK | T | SEQ ID NO.22 |
| BMV | | VDGVAGCGK | T | SEQ ID NO.23 |
| CMV | | VDGVAGCGK | T | SEQ ID NO.24 |
| ToMV | | VDGVPGCGK | T | SEQ ID NO.25 |

Abbreviations:
SV40- simian virus 40;
TGMV- tomato golden mosaicvirus;
BGMV- bean golden mosaic virus;

TABLE 1-continued

Consensus Amino Acid Sequence Among Viral Replication Proteins

ACMV- African cassava mosica virus;
BCTV- beet curely top virus;
CSMV- chloris striate mosica virus;
WDV- wheat dwarf virus;
MSV- maize strak virus;
CaMV- cauliflower mosaic virus;
PPV-NAT- aphid non-transmissible plum pox virus;
TEV- tobacco etch virus;
TVMV- tobacco vein mottling virus;
PVY-N -potato virus Y-N strain;
JGNMV- johnson grass mosaic virus;
PLRV- potato leafroll virus;
BNYVV- bean necrotic yellow vein virus;
PVX- potato virus X;
TMV tobacco mosaic virus;
AlMV- alfalfa mosaic virus;
BMV- brome mosaic virus;
VMC- cucumber mosaic virus;
ToMV- tobacco mosaic virus (tomato strain).

Trans-dominant mutations of genes encoded by plant viruses which are required for replication of the viral genome could potentially interfere with virus replication in whole plants, and therefore protect them from infection. Prior to the present invention, too little was known about how plant viral proteins involved in replication actually functioned to predict with any degree of certainty what sequences (if any) could be modified to create a trans-dominant variant that would interfere with that function. For most of these proteins all that was known is that they were required for viral replication. The exact role they played in the process of viral replication had not been elucidated. Previously, it was also unclear which proteins and molecules they interacted with in the plant cell, and whether or not they would bind to viral DNA or RNA.

One group of viruses which has been characterized in this manner is the geminivirus group. Geminiviruses are unique among plant viruses in both their twin isometric particles (18–20 nm in diameter) and their genomes, which comprise single-stranded circular DNAs. The genome can be a single component as in the leaf-hopper transmitted maize streak virus (MSV) or two components as in the white fly-transmitted tomato golden mosaic virus (TGMV). As a group, geminiviruses infect both monocotyledenous plants and dicotyledenous plants.

TABLE 2

Origins, vectors and hosts of 16 geminivirus isolates

| Virus | Abbreviation | Origin | Vector | Host | Reference |
|---|---|---|---|---|---|
| Abutilon mosaic | AbMV | Brazil | *Bemisia tabaci* | Malvaceae | Frischmuth et al. (1987) |
| Beet curly top | BCTV | California, U. S. A. | *Neoaliturus tenellus* | 44 families* | Stanley et al. (1986) |
| Bean golden mosaic | BGMV-PR | Puerto Rico | *B. tabaci* | Leguminosae, Malvaceae | Howarth et al. (1985) |
|  | BGMV-BZ | Brazil | *B. tabaci* | Leguminosae | Gilbertson et al. (1988) |
| Cassava latent† | CLV | Kenya | *B. tabaci* | Solanaceae | Stanley & Gay (1983) |
| Chloris striate mosaic | CSMV | Australia | *Nesoclutha pallida* | Gramineae | Andersen et al. (1988) |
| Digitaris streak | DSV | Vanuatu | *Nesoclutha declivata* | Gramineae | Donson et al. (1987) |
| Maize streak | MSV-K | Kenya | *Cicadulina spp.* | Gramineae | Howelll (1984) |
|  | MSV-N | Nigeria | *Cicadulina spp.* | Gramineae | Mullineaux et al. (1984) |
|  | MSV-S | South Africa | *Cicadulina spp.* | Gramineae | Lazarowitz (1988) |
| Mung bean yellow mosaic | MYMV | Thailand | *B. tabaci* | Leguminosae | Morinaga et al. (1987) |
| Tomato golden mosaic | TGMV | Brazil | *B. tabaci* | Solanaceae | Hamilton et al. (1984) |
| Tomato yellow leaf curl | TYLCV | Israel | *B. tabaci* | Solanaceae | N. Navot & H. Czosnek (unpublished) |
| Wheat dwarf | WDV-C | Czechoslovakia | *P. alienus* | Gramineae | Commandeur et al. (1987) |
|  | WDV-CJI | Czechoslovakia | *P. alienus* | Gramineae | Woolston et al. (1988) |
|  | SDV-S | Sweden | *P. alienus* | Gramineae | MacDowell et al. (1985) |

*All 44 families which contain hosts of BCTV are dicotyledonous (Bennett, 1971).
†Cassava latent virus is the same as African cassava mosaic virus (ACMV) (Bock & Woods, 1983).

Geminiviruses are divided into two sub-groups A and B, both with characteristic geminate particles. Sub-group A is the Maize streak virus sub-group, with the type member being the maize streak virus (MSV). The ssDNA genome is monopartite. Sub-group members are transmitted by the leafhopper in a persistant manner. Sub-group B is the African cassava mosaic sub-group, with the type member being the African cassava mosaic virus (ACMV). Members are similar to those of sub-group A, but their isometric particles contain a ss-DNA bipartite genome. Sub-group members are transmitted in nature by the whitefly in a persistant manner. Other members of this sub-group include bean golden mosaic, mung bean yellow mosaic, tobacco leaf curl, and tomato golden mosaic virus.

Tomato golden mosaic virus (TGMV) replicates in the nucleus of infected cells, from which duplex replicative forms can be isolated and cloned. The complete nucleotide sequence of TGMV has been determined (Hamilton et al., EMBO J. 3, 2197 (1984)). TGMV contains two genomic components, known as A and B. The A component contains a gene which encodes a protein required for viral replication. This same gene also contains the -Gly1-Xaa1-Xaa2-Xaa3-Xaa4-Gly2-Lys- (SEQ ID NO. 1) amino acid consensus sequence discussed above, which has been identified and designated as AL1. This gene served as the target for modifications taught by the present invention.

Preferred modifications of the -Gly1-Xaa1-Xaa2-Xaa3-Xaa4-Gly2-Lys- (SEQ ID NO. 1) include: 1) a deletion of the second Gly and insertion therefor of the amino acid sequence Ala-Leu-Glu, to generate the sequence -Gly1-Xaa1-Xaa2-Xaa3-Xaa4--Ala-Leu-Glu-Lys- (SEQ ID NO. 26), which is designated AL1ATPVAR.1; and 2) a deletion of the amino acid sequence -Xaa2-Xaa3-Xaa4-Gly2- and insertion therefor of the amino acid sequence -Thr-Leu-Glu- to generate the sequence -Gly$_1$-Xaa1-Thr-Leu-Glu-Lys- (SEQ ID NO. 27), which is designated AL1ATPVAR.2.

The determination of which modifications can be made that will confer protection against viral infection when expressed in transgenic plants can be determined through experimentation as set forth below. Modifications may be duplicated in any desired plant viral gene. Other modifications embodied by the present invention may be identified by one or more of the following methods.

Although the mechanism of protection is unknown, it is predicted that the modified protein expressed from the modified gene interferes with the function of its unmodified counterpart. Since the modifications occur in a region implicated in NTP binding/hydrolysis, interference might result from a loss or alteration of NTP binding/hydrolysis activity in the modified protein. While the conferred protection is primarily effective against the virus from which the modified gene is derived, it may extend to other related viruses.

Several in vitro assays may be useful for identifying the desired modifications. These assays are based upon the prediction that proteins encoded by the modified genes of the present invention act by interfering with a function of their unmodified counterparts. This type of interference may be screened for in vitro by adding the modified proteins to an assay which detects an activity provided for by the unmodified protein. An addition resulting in a loss of activity would indicate that the added modified protein is one which generates the trans-dominant effect.

The foregoing types of screens depend upon the development of in vitro activity assays for the unmodified proteins which form the basis of the present invention. These proteins are known to participate in the replication of their respective viral genomes. Many activities related to replication which these proteins may possess may be assayed for in vitro, including replicase, RNA polymerase, reverse transcriptase, helicase, ATP or GTP hydrolysis, primase, and nucleic acid binding or nicking activities. Applying these assays, one skilled in the art could determine whether the unmodified viral proteins which form the basis of the present invention contain one or more of the enumerated activities. Once an assayable activity has been identified for a particular viral protein, interference of that activity can be determined as described above. It is to be understood that different functions or activities may reside in different domains of the various proteins.

Assaying modified proteins for NTP binding activity may also reveal those which are embodied in the present invention. As previously discussed, protection from viral infection by the modified proteins may be due to a loss of NTP binding activity. Such a loss of activity may be detected by assaying the modified proteins (and their unmodified counterparts) for the ability to bind radiolabelled NTP's in vitro. This type of assay has been successfully used to detect NTP binding by TMV replicase and many proteins with ATPase activity.

The modified genes may also be screened by assay of transgenic callus. For this the modified genes are engineered for expression in plant cells and then transformed into tissue from a host plant of the virus for which protection is desired. From this tissue clonal transgenic callus expressing the modified gene is propagated. This callus is then challenged with an inoculum of the virus from which the modified gene is derived and assayed for viral replication. Inhibition of replication in a transgenic line suggests that the modified gene it expresses is trans-dominant.

Screening may also be performed with transgenic plants, and is the preferred assay for the present invention. Such plants expressing the modified gene can be regenerated from transgenic callus obtained as described in the preceding paragraph. These plants or their progeny may be challenged with an inoculum of the virus from which the modified gene is derived and assayed for development of viral infection. Delay or inhibition of viral infection in a transgenic plant (or its progeny) indicates that the modified gene it contains is trans-dominant.

In a preferred embodiment of the invention, the -Gly1-Xaa1-Xaa2-Xaa3-Xaa4-Gly2-Lys- (SEQ ID NO. 1) sequence is from TGMV AL1. TGMV AL1 was originally identified as a 1056 nucleotide (352 amino acid) open reading frame (ORF) from the sequence of the TGMV A component genome. Mutational analysis of the TGMV A genome indicated that this was the only viral ORF required for replication of TGMV (Elmer, 1988). The AL1 ORF from TGMV has been engineered for expression in transgenic plants under the direction of the CaMV35S promoter and the CaMVe35S promoter. Plants transformed with this chimeric gene have been obtained which produce the AL1 protein. Analysis of these plants has revealed that the AL1 protein produced can functionally interact with the TGMV genome and that this viral protein is not only required, but sufficient for replication of the TGMV genome in the presence of host plant proteins (Hanley-Bowdoin, 1990). However, the exact function of the AL1 protein as it relates to TGMV replication is unknown.

It is possible that this -Gly1-Xaa1-Xaa2-Xaa3-Xaa4-Gly2-Lys- (SEQ ID NO. 1) sequence functions in these plant viral gene products in the same way that it functions in the SV40-TAg. This possibility is supported by two factors. First, this sequence has been found in several distinct classes of proteins in association with a common activity, ATP binding/catalysis. Second, the TAg and these plant viral proteins are all involved in the replication of their respective viral DNAs. For TAg, its role in viral replication involves a helicase activity requiring ATP hydrolysis (Stahl, 1986). The role of these plant viral proteins in replication may also be coupled with ATP catalysis in a similar manner.

If the -Gly1-Xaa1-Xaa2-Xaa3-Xaa4-Gly2-Lys- (SEQ ID NO. 1) sequence does perform a common function in these proteins, specific mutations in this sequence which act in a trans-dominant manner for the TAg gene may act the same way in these plant viral genes. If so, then the expression of these mutant viral proteins in plants may protect them from infection with the respective virus by interfering with viral replication. Depending on the mechanism by which interference occurs, which is unknown, a mutant may interfere only with the virus from which it was derived or it may interfere more generally with all plant viruses or a related subset.

A plant viral genome may be isolated from a library recovered from purified geminivirus virions. The library may be constructed in a number of ways known to those of skill in the art. For example, the double stranded replicative form may be used to clone the AL1. Alternatively, the desired gene (here, AL1 from TGMV) may be synthesized from a known sequence. The nucleotide sequence of the AL1 gene may be modified at the 5' and 3' ends to facilitate cloning. This may be accomplished by site- directed mutagenesis, using the method described by Kunkel (1985), and may provide different restriction sites as needed. Various oligonucleotide primers may be used to modify the 5' and 3' ends. Multilinkers may be utilized, which facilitate ordered assembly of the heterologous DNA sequence.

Sequencing of the respective gene may be performed by the method of Sanger and Coulson, *Proc. Nat'l Acad. Sci.* 74: 5463–5467 (1977) using a Sequenase ® product, according to the manufacturer's instructions. All peptide structures represented are shown in conventional format wherein the amino group at the N-terminus appears at the left and the carboxyl group at the C-terminus at the right.

It is understood that the particular nucleotide and/ or amino acid sequences disclosed herein are representative in the sense that equivalent genes or portions thereof may be obtained and/or generated pursuant to this disclosure. By equivalent it is meant that said gene or portion thereof would function in a manner substantially the same as the gene disclosed herein, and would provide viral resistance to a plant in substantially the same manner.

A structural DNA sequence encoding the modified viral AL1 gene may be inserted into a plant transformation vector. A gene is defined as an element or combination of elements that are capable of being expressed in a cell, either alone or in combination with other elements. In general, a gene comprises (from the 5' to the 3' end): (1) a promoter region which includes a 5' non-translated leader sequence capable of functioning in plant cells; (2) a structural gene or structural DNA sequence which codes for the desired protein; and (3) a 3' non-translated region, which typically causes the termination of transcription and the polyadenylation of the 3' region of the RNA sequence. Each of these elements is operably linked to the adjacent element. A gene comprising the above elements may be inserted by standard recombinant DNA methods into a plant transformation vector. Some or all of the elements of the gene may be present, with additional or remaining elements added to the vector if necessary. A further aspect of the present invention is the introduction of multiple copies of the modified AL1 gene into the plant cell. Additionally, the plant transformation vector may be constructed with all of the elements present except for the structural gene, which may then be added at an appropriate time by known methods.

The segment of DNA referred to as the promoter is responsible for the regulation of the transcription of DNA into mRNA. A number of promoters which function in plant cells are known in the art and may be employed in the practice of the present invention. These promoters may be obtained from a variety of sources such as plants or plant viruses, and may include but are not limited to promoters isolated from the caulimovirus group such as the cauliflower mosaic virus 35S promoter (CaMV35S), the enhanced cauliflower mosaic virus 35S promoter (CaMVe35S) , the figwort mosaic virus full-length transcript promoter (FMV35S), and the promoter isolated from the chlorophyll a/b binding protein as is known in the art. Other useful promoters include promoters which are capable of expressing the replicase enzyme in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis- related proteins (e.g. PR-1a) , and wound-inducible protease inhibitor from potato would be useful.

Alternate promoters, such as the promoter from glutamine synthetase for expression in vascular tissues or promoters from epidermal cells, could be used to express the protein in certain cell types. The patatin promoter could be used to express the protein in the tuber. The particular promoter selected is preferably capable of causing sufficient expression of the modified AL1 structural gene to which it is operably linked to result in the production of an effective amount of the modified AL1 to provide viral resistance, but not so much as to be detrimental to the cell in which it is expressed. The promoters selected should be capable of functioning in tissues including but not limited to epidermal, vascular, and mesophyll tissues. The actual choice of the promoter is not critical, as long as it has sufficient transcriptional activity to accomplish the expression of the modified AL1 gene and subsequent conferral of viral resistance to the plants.

The non-translated leader sequence can be derived from any suitable source and can be specifically modified to increase the translation of the mRNA. The 5' non-translated region can be obtained from the promoter selected to express the gene, the native leader sequence of the gene or coding region to be expressed, viral RNAs, suitable eucaryotic genes, or a synthetic gene sequence. The present invention is not limited to the construct presented in the following Example. The non-translated leader sequence can also be derived from an unrelated promoter or viral coding region as described.

The structural DNA sequence which codes for the AL1 gene which is to be modified by way of the present invention may be isolated from any geminivirus using methods known to those of skill in the art as discussed earlier in this section. Other modifications to this gene may also be made, including modifications to the 5' or 3' termini of the structural gene, such as the introduction of an initiation codon at the 5' end.

The termination region or 3' non-translated region which is employed is one which will cause the termination of transcription and the addition of polyadenylated ribonucleotides to the 3' end of the transcribed mRNA sequence. The termination region or 3' non-translated region will be additionally one of convenience. The termination region may be native with the promoter region, native with the structural gene, or may be derived from another source, and preferably include a terminator and a sequence coding for polyadenylation. Suitable 3' non-translated regions of the chimeric plant gene include but are not limited to: (1) the 3' transcribed, non-translated regions containing the polyadenylate signal of *Agrobacterium* tumor-inducing (Ti) plasmid genes, such as the nopaline synthase (NOS) gene, (2) plant genes like the soybean 7S storage protein genes and the pea small subunit of the ribulose 1,5-bisphosphate carboxylase-oxygenase (ssRUBISCO) E9 gene and (3) the 3' termination region from the geminivirus utilized, or from any other virus.

In developing the expression construct, the various components of the expression construct or fragments thereof will normally be inserted into a convenient cloning vector which is capable of replication in a bacterial host, such as *E. coli*.

Numerous vectors exist that have been described in the literature. After each cloning, the vector may be isolated and subjected to further manipulation, such as restriction, insertion of new fragments, ligation, deletion, resection, insertion, in vitro mutagenesis, addition of polylinker fragments, and the like, in order to provide a vector which will meet a particular need. Once the construct is completed, it may then be transferred to an appropriate vector for further manipulation in accordance with the manner of transformation of the plant cell.

A variety of techniques are available for the introduction of the genetic material into or transformation of the plant cell host. However, the particular manner of introduction of the plant vector into the host is not critical to the practice of the present invention. Any method which provides for efficient transformation may be employed. In addition to transformation using plant transformation vectors derived from the tumor-inducing (Ti) or root-inducing (Ri) plasmids of *Agrobacterium*, alternative methods could be used to insert the DNA constructs of the present invention into plant cells. Such methods may include, for example, the use of liposomes, electroporation, chemicals that increase the free uptake of DNA, DNA delivery via microprojectile bombardment, microinjection, and transformation using viruses or pollen.

A plant transformation vector preferably includes all of the necessary elements for transformation of plant cells. Typical plant cloning vectors comprise selectable marker genes, scoreable marker genes, T-DNA borders, cloning sites, appropriate bacterial genes to facilitate the identification of transformants, broad host range replication and mobilization functions, and other elements as desired. The modified AL1 gene can be inserted into any suitable plant transformation vector for transformation into the desired plant species. Suitable plant transformation vectors include those derived from a Ti plasmid of *Agrobacterium tumefaciens*, in addition to those disclosed, for example, by Herrera-Estrella (1983), Bevan (1984), Klee (1985) and Fraley (1983).

Selectable marker genes may be used to select for those cells which have become transformed. Conveniently, the marker employed may be resistance to an antibiotic, such as kanamycin, G418, hygromycin, streptomycin, and the like. Other markers could be employed in addition to or in the alternative, such as, for example, a gene coding for herbicide tolerance such as tolerance to glyphosate, sulfonylurea, phosphinothricin, or bromoxynil. Additional means of selection could also be employed. The particular marker employed will be one which will allow for the selection of transformed cells as opposed to those cells which were not transformed. Depending on the number of different host species one or more markers may be employed, where different conditions of selection would be used to select the different host, and would be known to those of skill in the art.

Plant transformation vectors containing the modified AL1 gene may be used to transform plants of the *Solanaceae* family. In particular, infection by geminiviruses is a persistent problem in potato and can also infect tomato and tobacco. An *Agrobacterium*-mediated transformation protocol is known to be effective in transforming members of the *Solanaceae* family. When an Agrobacterium-mediated transformation is used, the desired transformation vector is mobilized into a suitable *Agrobacterium* strain. The ABI *Agrobacterium* strain is described for exemplary purposes. The desired transformation vector is mobilized into an ABI *Agrobacterium* strain by the triparental mating system using the helper plasmid pRK2013 (Ditta et al. 1980). The binary ABI strain is the chloramphenicol resistant derivative of *Agrobacterium tumefaciens* A208 which carries the disarmed Ti plasmid pTiC58 (Koncz and Schell 1986). The Ti plasmid does not carry the T-DNA phytohormone genes and the strain is therefore unable to cause crown gall disease. The disarmed Ti plasmid provides the trfA gene functions required for autonomous replication of the vector after conjugation into the ABI strain. When the plant tissue is incubated with the ABI::transformation vector conjugate, the vector is transferred to the plant cells by the vir functions encoded by the disarmed pTiC58 plasmid. The pTiC58 Ti plasmid does not transfer to the plant cells, but remains in the Agrobacterium. Either single- or double-border transformation vectors can be delivered to the plant by *Agrobacterium*. Single border vectors open at the right T-DNA border region, and the entire vector sequence is inserted into the host plant chromosome. The right border is lost during transfer and integration. In a double border vector, DNA between the right and left borders is inserted into the plant chromosome, thereby delivering only the chimeric genes of interest to the chromosome. The remainder of the vector, and the border sequences are lost during the transfer and integration.

Transformation and regeneration protocols for members of the *Solanaceae* family are known in the art. After the potato plant has been transformed and after transformed callus has been identified, the transformed callus tissue is regenerated into whole plants. Any known method of regeneration of potato plants can be used in this invention.

For tomato, the transformation protocol described in McCormick et al. (1986) can generally be used. The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. The regeneration of plants transformed by *Agrobacterium* from leaf explants can be achieved as described by Horsch et al., *Science* 227:1229–1231 (1985). In this procedure, transformants are grown in the presence of a selection agent and in a medium that induces the regeneration of shoots in the plant species being transformed as described by Fraley et al., *Proc. Nat'l. Acad. Sci. U.S.A.,* 80:4803 (1983). This procedure typically produces shoots within 2 to 4 months and these transformant shoots are then transferred to an appropriate root-inducing medium containing the selective agent and an antibiotic to prevent bacterial growth. Transformant shoots that are rooted in the presence of the selective agent to form plantlets are then transplanted to soil or other media to allow the production of roots. These procedures vary depending on the particular plant species employed, such variations being well known in the art.

A plant of the present invention containing the desired modified AL1 gene is cultivated using methods known to those of skill in the art. A transformed plant of the present invention thus is capable of expressing the modified AL1 gene and exhibits viral resistance thereby. The presence of the modified AL1 gene or gene product in the transformed plant may be determined by any suitable method known to those of skill in the art. Included in these methods are Southern, Northern, and Western Blot techniques, ELISA, and various bioassays. The transformed plant capable of expressing the modified AL1 gene may then be assayed for the determination of antiviral activity.

The following Example is provided to better elucidate the practice of the present invention and should not be interpreted in any way as to limit the scope of the present invention. Those skilled in the art will recognize that various modifications can be made to the methods and genes described herein while not departing from the spirit and scope of the present invention. For the sake of clarity and brevity of explanation, the following description of the particular embodiments will again be exemplified by the use of tomato golden mosaic virus (TGMV).

EXAMPLE

General information pertinent to the Example:

Media, Buffers, and Solutions

MSO
MSO+KAN300
LBSCK contains 10 g NaCl, 5 g yeast extract, 10 g Bacto-Tryptone, 50 mg spectinomycin, 25 mg chloramphenicol and 50 mg kanamycin in a 1 liter volume, pH 7.0.
MSO contains 4.4 g MX salts (Sigma Chemical Co., St. Louis, Mo.), 30 g sucrose and 2 ml $B_5$ vitamin (500X) in a 1 liter volume, pH 5.7.
PM media contains 4.4 g MS salts (Sigma Chemical Co., St. Louis, Mo.), 30 g sucrose, 0.17 g $NaH_2PO_4 \cdot H_2O$, 1 ml thiamine HCl and 0.1 g inositol in a 1 liter volume, pH 6.0 and 0.2% Gelrite agar.
shoot induction media contains MSO plus 5.0 mg/l ZR, 10 mg/l $AgNO_3$ and 0.3 mg/l $GA_3$ (gibberellic acid) and 100 mg/l kanamycin.
callus induction plates contains MSO plus 3.0 mg/l BA (6 benzylaminopurine) and 0.01 mg/l NAA.
callus induction media contains 5 mg/l Zeatin Riboside, 10 mg/l $AgNO_3$,, and 0.1 mg/l NAA.
NAA is naphthaleneacetic acid.
Davis germination media contains 4.3 g/l MS salts, 20g/l sucrose and 10 mls/l Nitsch vitamins, pH 5.8.
Davis regeneration media contains 1X MS salts, 3% sucrose, 1X Nitsch vitamins, 2.0 mg/l zeatin, pH 5.8.
Nitsch vitamin solution contains 100 mg/l myo-inositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine.
MSP-5 contains 4.4 g MS salts (Sigma), 5 ml SLLX vitamins (200x), 30 g sucrose, 2.25 ml BAP, 0.186 ml NAA in 1 liter, pH 5.6 and 0.2% Gelrite agar.
LB media contains 10 g tryptone, 5 g yeast extract and 5 g NaCl per liter; optionally with 25 µg/ml chloramphenicol and 50 mg kanamycin.
Unless otherwise specified, the above solutions represent the basic (1x) concentration employed. Throughout the Examples, where different concentration levels are employed, that fact is indicated by referring to the solution as a multiple of the basic (1x) concentration.

Mutagenesis of TGMV AL1 and Construction of Plasmids

Mutations in the TGMV AL1 gene were made by site-directed mutagenesis using a MUTA-GENE ® in-vitro mutagenesis kit (Bio-Rad). Both mutations were performed on a derivative of pUC119 known as pMON434, which contains a HindIII insertion of a modified TGMV A component genome. The TGMV A genome in pMON434 had been previously modified in the following way:
1) HindIII linkers (5' CAAGCTTG 3') had been added to the ScaI site and used to clone the A component into the HindIII site of pUC119; 2) The AsuII site had been filled in, SacI linkers (5' CGAGCTCG 3, ) added, and religated using SacI (this modification also created two NruI sites on either side of the new SacI site); and 3) A BglII and NdeI site had been introduced into the region directly upstream of the AL1 coding sequence by site- directed mutagenesis. The mutagenesis resulted in the insertion of six nucleotides (shown in bold) into the following native sequence shown from nucleotide #37-#1 of the TGMV A map:

```
37                                                    1
5' -GTAGTAAGCCAGATCTTAATTACAAAACATATGCCATCGC- 3'
(SEQ ID NO.28)
```

The oligonucleotide primers used to make mutations in the AL1 gene of pMON434 consisted of the sequences shown below. Sequences homologous to the native TGMV A sequence are shown in plain type, while non-homologous sequences are shown in bold type. It should be noted that these non-homologous sequences contain an XbaI restriction site. The positions of the starting and ending nucleotides on the TGMV A map are also indicated.
Mutagenesis oligomer 1 (pMON 1648):
(1931) ATAGTCGGACGGCTCTAGAGAAGACTATGT (1908)    (SEQ    IDNO.29)    N-term -SerArgThrAlaLeuGluLysThrMet-
Mutagenesis oligomer 2 (pMON 1632, 1634):
(1940) TCGAGGGCGATACTCTAGAGAAGACTATGT (1908)    (SEQ    ID    NO.    30)    N-term -GluGlyAspThrLeuGluLysThrMet-
The pMON434 derivatives created by mutagenesis with these oligomers are pMON1646 and pMON1629, respectively.

Triparental Mating Procedure

The following protocol was used for all plasmids. A generic plasmid designation of PMONX is used to encompass all pMON plasmids of this invention. Plasmids pMON1648, pMON1632, and pMON1634 were used here.
Prior to transformation, E. coli containing pMONX were mated into Agrobacterium ABI by a triparental mating with the helper plasmid pRK2013 (Ditta et al. 1980). ABI is the A208 Agrobacterium tumefaciens strain carrying the disarmed pTiC58 plasmid pMP9ORK (Konez and Schell, 1986). The disarmed Ti plasmid provides the trfA gene functions that are required for autonomous replication of the pMON vector after the conjugation into the ABI strain. When plant tissue is incubated with the ABI/pMON conjugate, the vector is transferred to the plant cells by the vir functions encoded by the disarmed pMP9ORK Ti plasmid. Agrobacterium were grown for 30 hours in LB media (10 g tryptone, 5 g yeast extract, and 5 g NaCl per liter) with 25 µg/ml chloramphenicol and 50 mg kanamycin at 30° C. E. coli containing pRK2013 were grown overnight in kanamycin (50 µg/ml). This culture was started with several colonies. E. coli with PMONX were grown in LB with 75 µg/ml spectinomycin. After all of the cultures were grown, 4 ml of LB was added to a tube with 100 µl each of Agrobacterium ABI, pRK2013, and pMONX. This mixture was centrifuged in a microfuge for 5 minutes and the supernatant fraction decanted. The pellet fraction was resuspended in the remaining liquid, and an aliquot was pipetted into the center of an LB plate. After overnight growth at 30° C., an aliquot of cells from this plate was streaked onto an LB plate supplemented with 75 µg/ml spectinomycin, 50 µg/ml kanamycin and 25 µg/ml chloranmphenicol.
After 24–48 hours at 30° C., the plate from the triparental mating of PMONX, pRK2013 and Agrobacterium ABI contained colonies, while the control plate from the mating of PMONX and ABI (without pRK2013, which is required for mobilization) did not contain colonies. After the triparental mating, 4 colonies were selected from the former plate, inoculated into a liquid culture of LB supplemented with 75 µg/ml spectinomycin, 50 µg/ml kanamycin and 25 µg/ml chloramphenicol and grown at 30° C. The presence of 0the modified AL1 gene was shown by restriction analysis of *Agrobacterium* DNA. One of the cultures verified to contain the modified AL1 gene was used for transformation of tobacco.

Transfomation

Figure 5:
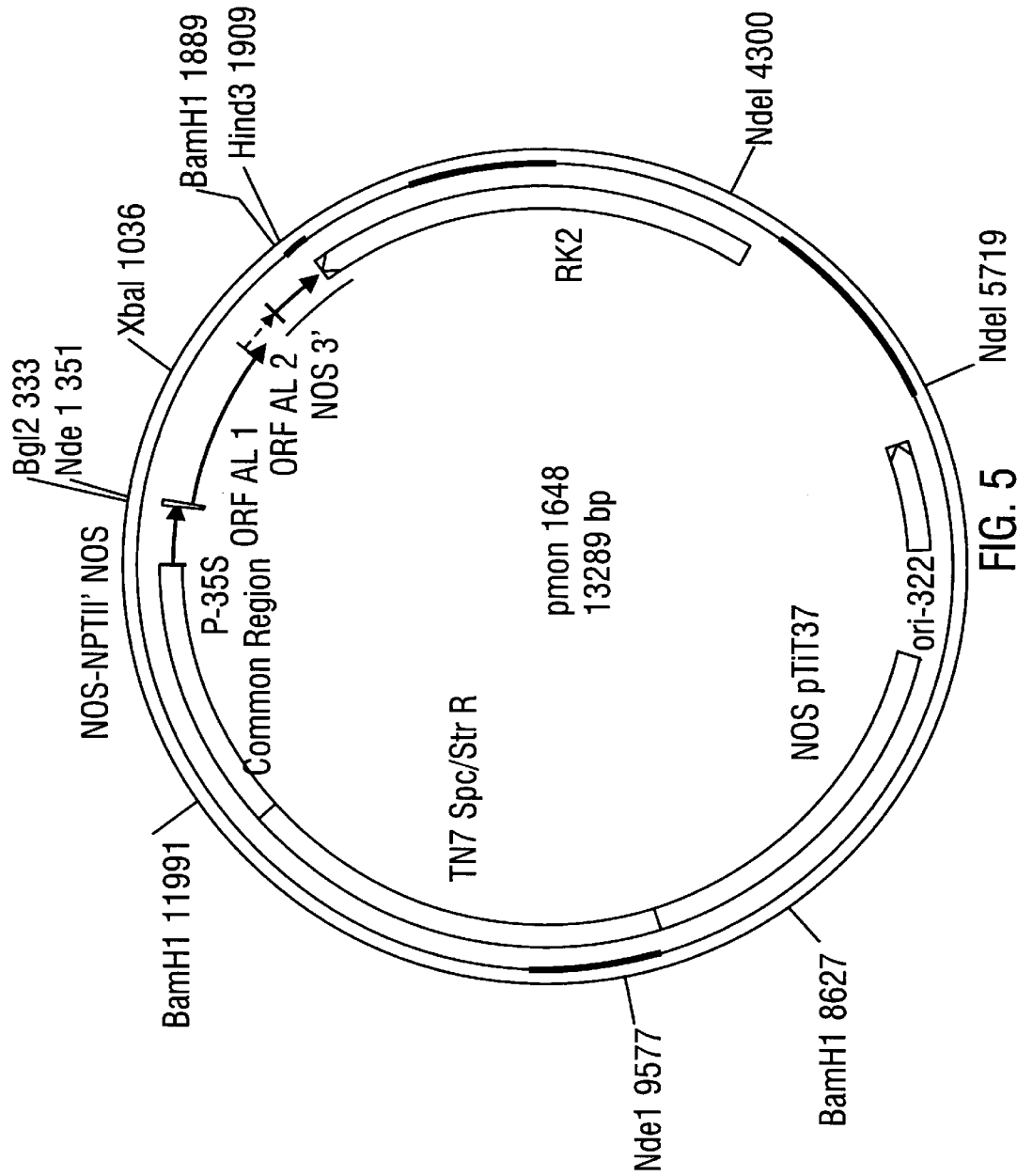
FIG. 5 illustrates pMON1648.
Figure 6:
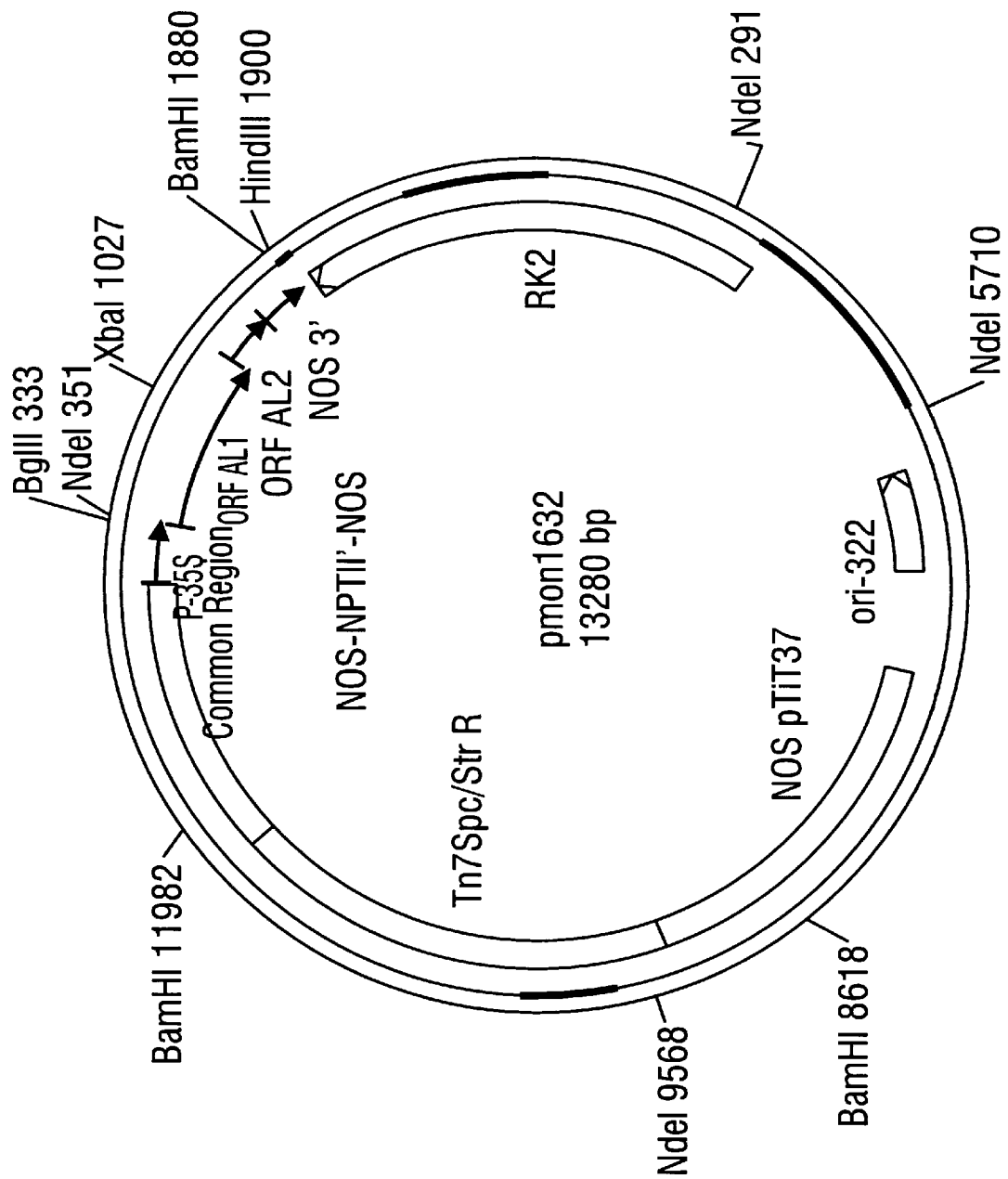
FIG. 6 illustrates pMON1632.
Figure 7:
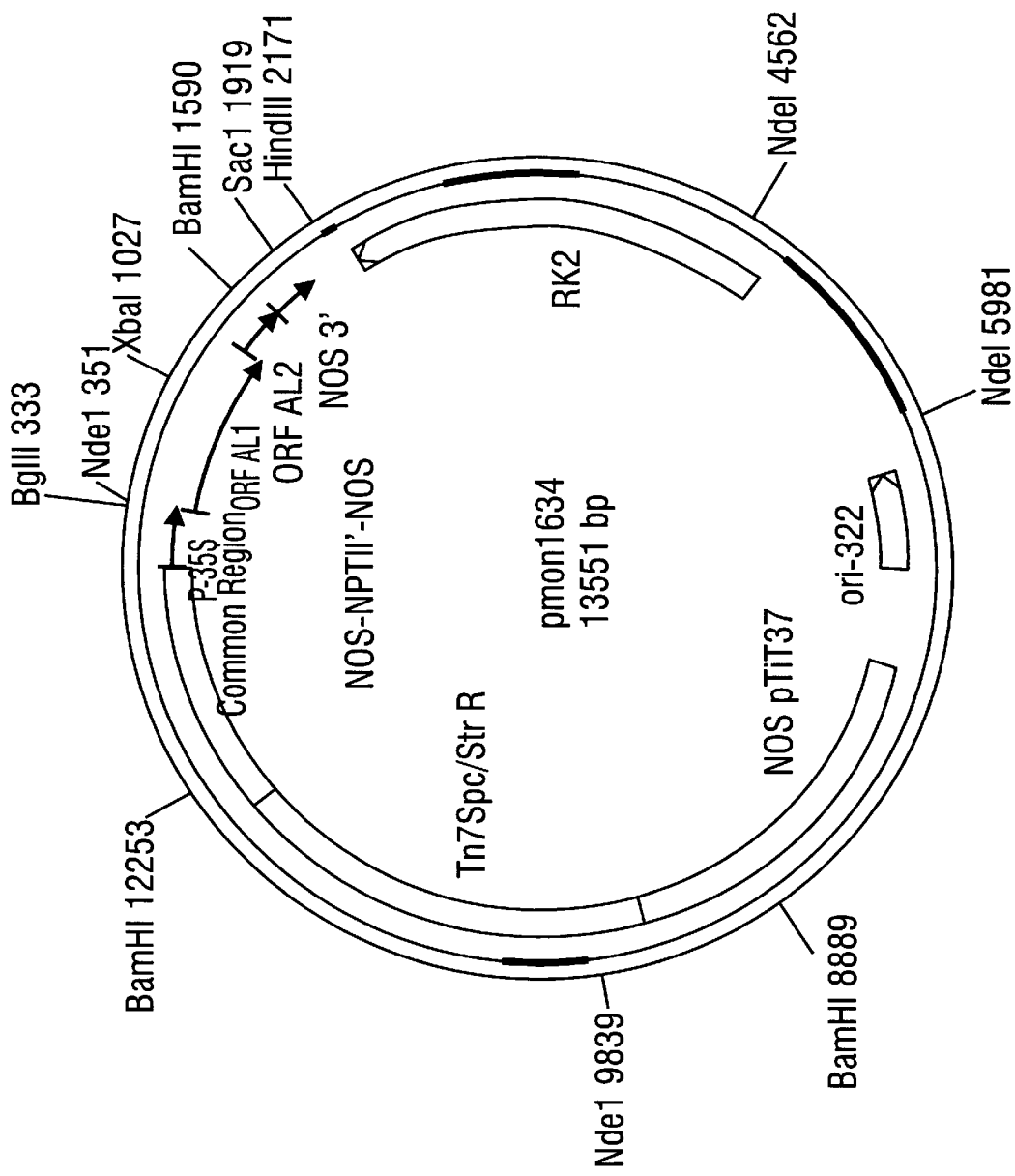
FIG. 7 illustrates pMON1634.
Figure 8A:
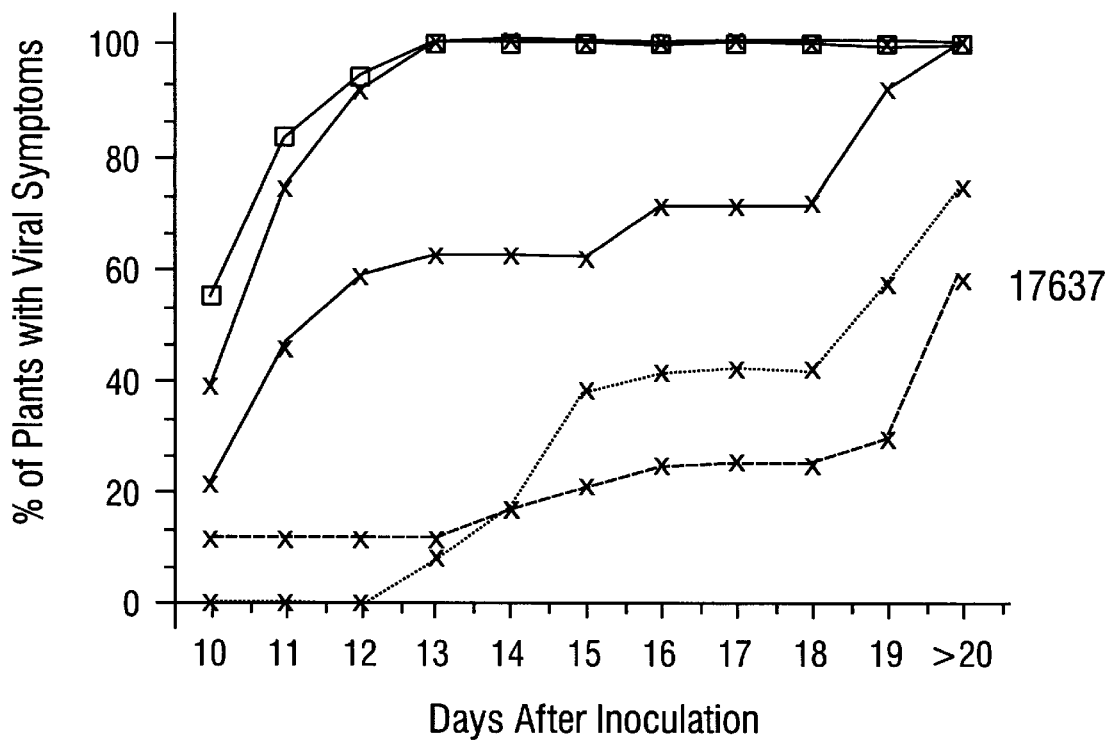
FIGS. 8A–8C illustrate infectivity data using pMON1632, pMON1634, and pMON1648. Transgenic lines exhibit reduced infectivity. Wild type and transgenic N. benthamiana plants were agroinoculated with Tomato Golden Mosaic Virus and scored for the appearance of viral symptoms. Results are shown as the percentage of plants which appeared infected on successive days after agroinoculation. In each graph wild type infectivity results are represented by the line connecting the dark boxes. All other plant lines represent results obtained for transgenic progeny from independent transgenic plants containing the constructs designated at the top of each panel. For each panel the line exhibiting the highest degree of inhibition is designated at right.
Figure 8B:
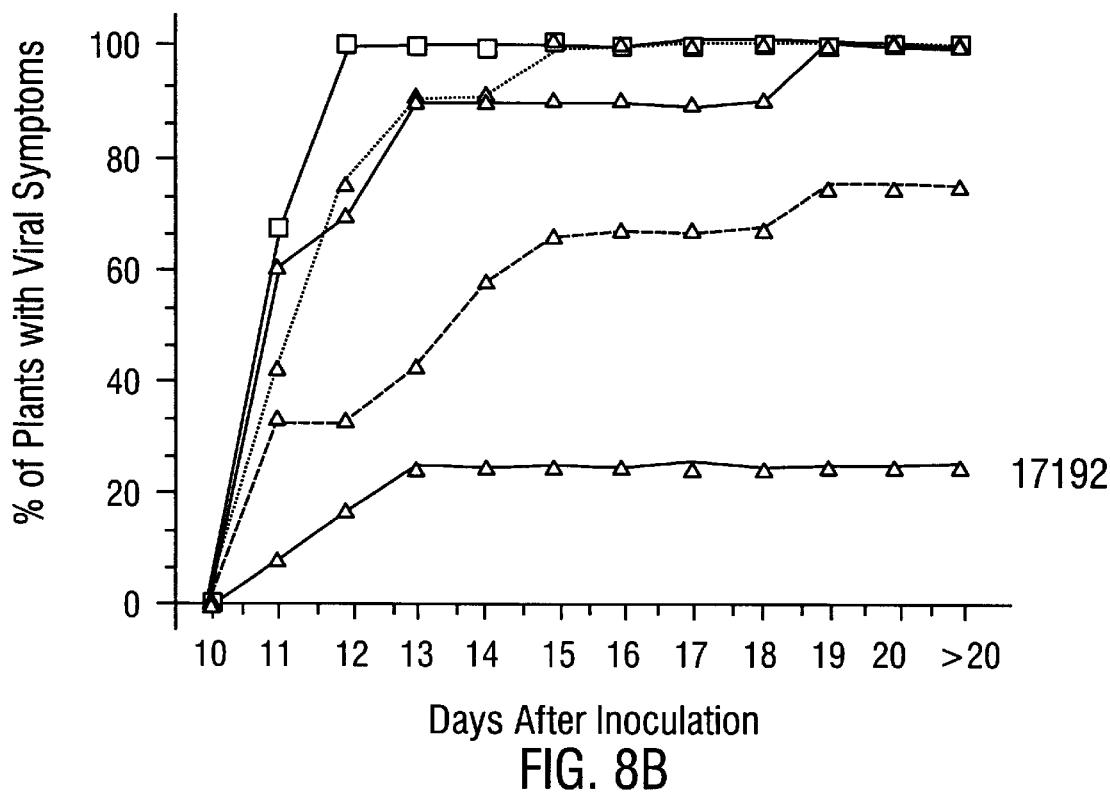
Figure 8C:
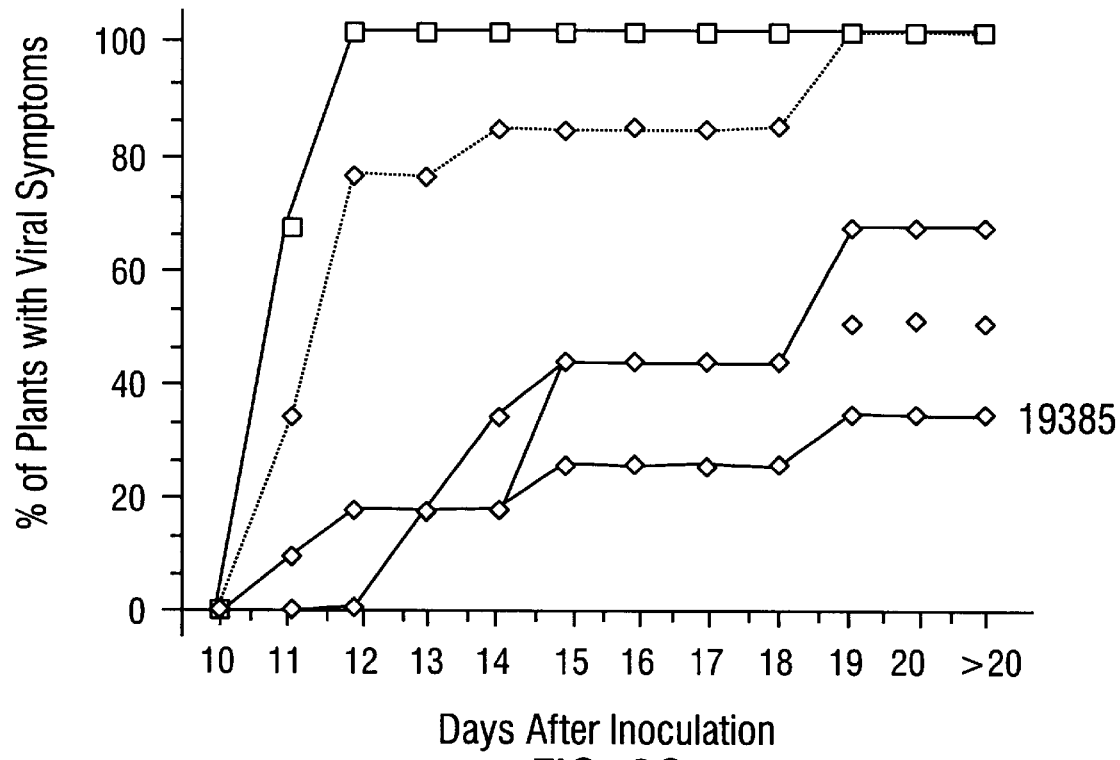

Mutant AL1 coding sequences were inserted into the plant transformation vector pMON530 to create a chimeric CaMV35S/AL1/NOS 3' gene for expression in plants. For pMON1646, a 1.2 kb BglII-BamHI fragment was inserted into the BglII site of pMON530 to create pMON1648 (FIG. 5). For pMON1629, a 1.8kb BglII-HindIII fragment was inserted into pMON530 digested with BglII and HindIII to create pMON1634 (FIG. 7). pMON1634, pMON1632, and pMON1648 were mated into *Agrobacterium* strain GV3111SE using the triparental mating procedure (Ditta et al.). pMON1632 is shown in FIG. 6. *Agrobacterium* containing these constructs was then used to transform *Nicotiana benthamiana* (tobacco) plants (Horsch, 1985).

Infection Experiments

Transgenic plants containing pMON1634 were first obtained and screened for infectivity once before plants containing pMON1648 were obtained. In this experiment approximately 12 progeny of each transgenic were tested. Each plant was inoculated with 100 ng of purified TGMV particles by rubbing the inoculum onto two Carborundum treated leaves. Out of 7 transgenic lines that were tested, 3 showed significantly reduced frequencies of infection compared to the wild type control. The two lines which showed the lowest infection frequencies, #17192 (11% infected) and #17182 (25% infected) were retested in a later infectivity experiment.

Figure 10A:
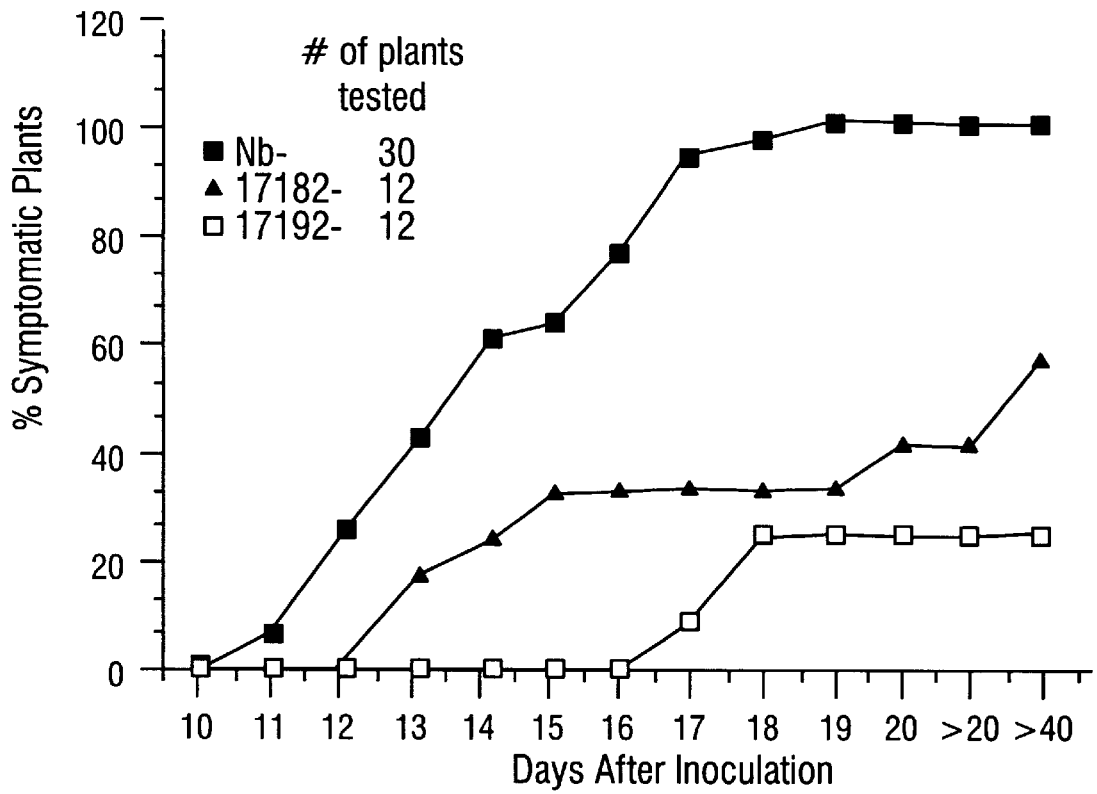
FIG. 10 illustrates infectivity data with pMON1634.
Figure 10B:
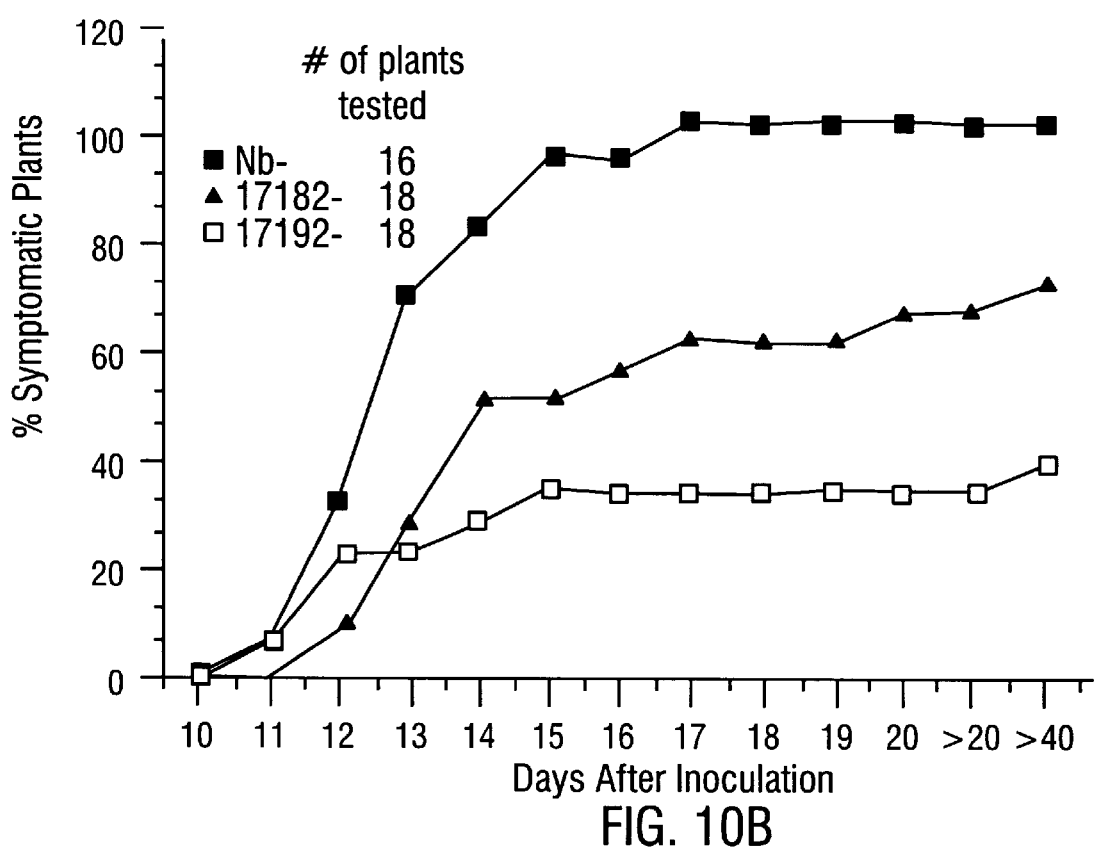
Figure 10C:
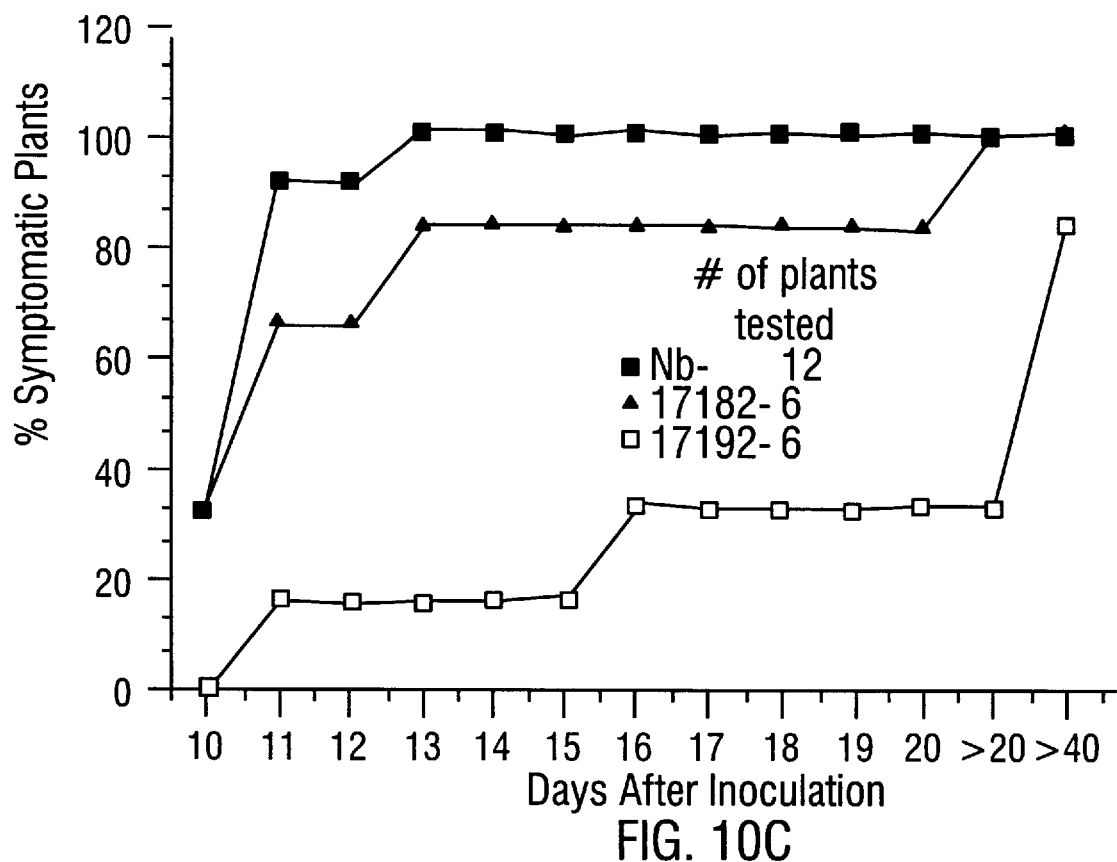
Figure 11:
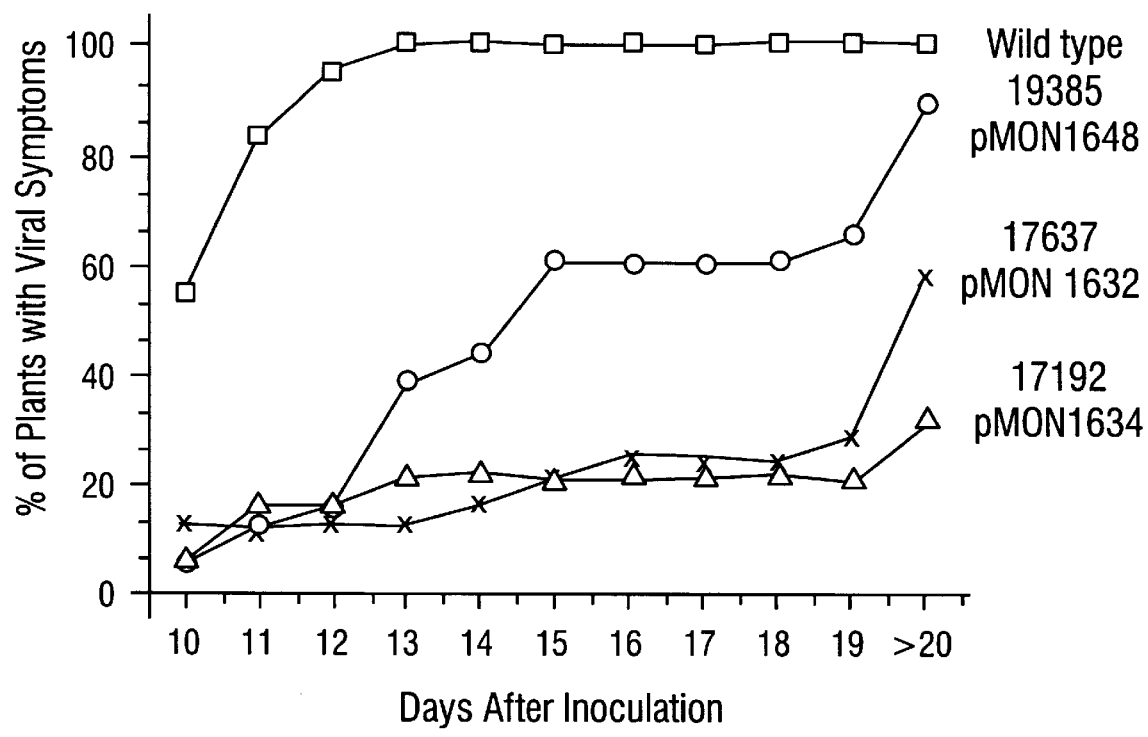
FIG. 11 illustrates infectivity data using best pMON1632, pMON1634, and pMON1648.

The two pMON1634 transgenic lines used in this experiment, #17192 and #17182, were germinated on MSO media without kanamycin because earlier germination results indicated that virtually 100% of the seed from these two primary transgenics were kanamycin resistant which contained multiple copies of pMON1634. As the graphs in FIG. 10 show both lines exhibited discernible levels of protection, with the 17192 line being better than the 17182 line. The 17192 line appears to be protected from agroinoculation of TGMV as well as pure virus inoculation. Also, crude extracts were made from several of these plants 19 days after inoculation and used to make duplicate dot blots. These blots were hybridized with TGMV A and B specific probes. Extracts from symptomatic plants contained easily detectable levels of both virus component while those from nonsymptomatic plants did not contain detectable levels of either virus component.

Figure 9:
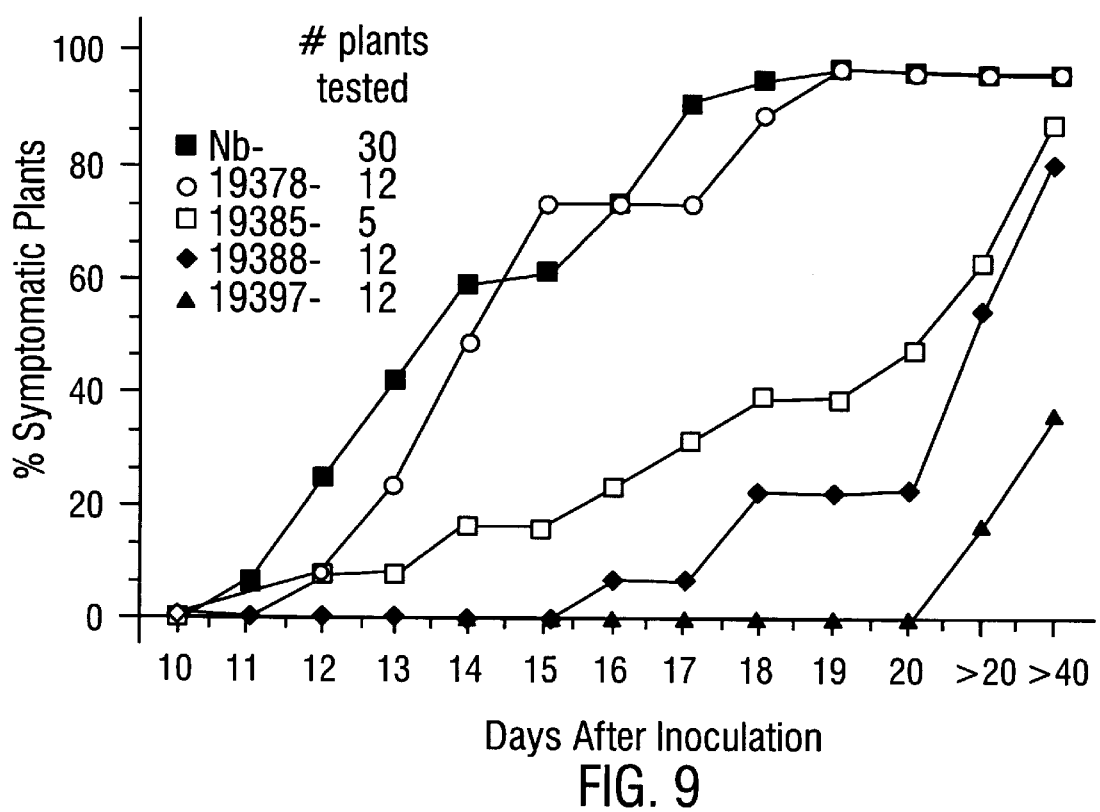
FIG. 9 illustrates infectivity data with pMON1648.

Transgenic plants containing pMON1648 were also tested. The seed was collected from these primary transgenics and germinated on MSO+KAN300. From the infectivity results shown in FIG. 9, 3 out of the 5 lines tested showed some level of protection. Dot blots were also performed on these plants.

Detection of AL1 mutant protein

Concentrated protein extracts have been made using pooled leaf tissue from the 17182 and 17192 transgenic lines. Using the standard Western blot procedure, a protein of the expected size which cross reacts with antibody against the AL1 protein was detected in the 17192 extract. The same procedure was used to detect AL1 protein in pMON1648 transgenic lines which exhibited positive protection results.

All publications and patent applications mentioned in this specification are indicative of the level of skill of those skilled in the art to which this invention pertains.

From the foregoing, it will be seen that this invention is one well adapted to attain all the ends and objects hereinabove set forth together with advantages that are obvious and that are inherent to the invention. It will be understood that certain features and sub-combinations are of utility and can be employed without reference to other features and sub-combinations. This is contemplated by and is within the scope of the claims. Because many possible embodiments can be made of the invention without departing from the scope thereof, it is to be understood that all matter herein set forth or shown in the accompanying drawings is to be interpreted as illustrative and not in a limiting sense.

REFERAENCES

1. Abel et al. (1986) *Science* 232: 738–743.
2. Auborn, K. et al., (1989) *J. of Virol.*, 63: 912–918.
3. Boroweic, J. A. et al.,(1988) *PNAS*, 85: 64–68.
4. Bradley, M. K. et al, (1984) *PNAS*, 71: 3754–3764.
5. Bradley, M. K. et al., (1987) *PNAS*, 84: 4026–4030.
6. Buck et al. PCT publication WO 92/03539.
7. Clark R. et al., (1983) *Mol. Cell. Biol.*, 3: 220–228.
8. Cuozzo et al. (1988) *BioTechnol.* 6: 549–557.
9. Ditta G. et al., (1980) *PNAS*, 77: 7347–7351.
10. Elmer J. S. et al., (1988) *Nucleic Acids Res.*, 16: 7043–7060.
11. Elmer J. S. et al., (1988) *Plant Mol. Biol.*, 10: 225–234.
12. Farber J. M. et al, (1987) *J. Virol.*, 61: 436–445.
13. Fraley et al. (1983) *Proc. Natl. Acad. Sci. USA* 80: 4803–4807.
14. Golemboski et al. (1990) *Proc. Natl. Acad. Sci. USA* 87: 6311–6315.
15. Hanley-Bowdoin, L. et al., (1990) *PNAS*, 87: 1446–1450.
16. Hamilton et al., (1984) *EMBO J.* 3,2197.
17. Hemenway et al. (1988) *EMBO J.* 7: 1273–1280.
18. Hodgman (1988) *Nature* 333: 22–23.
19. Horsch, R. B. et al., (1985) *Science*, 227: 1229–1231.
20. Howarth, A. J. et al.,(1989) *J. Gen. Virol.*, 70: 2717–2727.
21. Ishikawa et al. (1986) *Nucleic Acids Res.* 14: 8291–8305.
22. Kaniewski et al. (1990) *Biotechnol.* 8:750–754.
23. Kelly, T. J. et al., (1988) *J. Biol. Chem.*, 263: 17889–17892.
24. Koncz and Schell (1986) *Mol. Gen. Genet.* 204: 383–396.
25. Kunkel (1985) *Proc. Natl. Acad. Sci. USA* 82: 488–492.
26. Lawson et al. (1990) *BioTechnol.* 8: 127–134.
27. Loeber, G. et al., (1989) *J. Virol.*, 63: 4426–4430.
28. Manos, M. M. et al., (1985) *J. Virol.*, 53: 120–127.
29. Mc Cormick et al. (1986) *Plant Cell Reports* 5: 81–84.
30. Rogers, S. G. et al., (1986) *Cell*, 45: 593–600.
31. Sanger and Coulson, (1977) *PNAS* 74:5463–5467.
32. Serrano, R. et al., (1989) *Plant Mol. Biol.*, 40: 61–94.
33. Stahl, H. et al., (1986) *EMBO*, 5: 1939–1944.
34. Stark and Beachy (1989) *BioTechnol.* 7: 1257–1262.
35. Taschner et al. (1991) *Virology* 181: 445–450.
36. Tumer et al. (1987) *EMBO J.* 6:1181–1188.
37. van Dun et al. (1988) *Virology* 163: 572–578.
38. Zhu, J. et al., (1989) *J. Virol.*, 63: 4777–4786.

We claim:

1. An isolated DNA molecule which comprises a structural gene encoding a modified form of an AL1 protein normally required for the replication of a gemini virus of tomato wherein the unmodified AL1 protein is a protein which has an activity associated with it of the type selected from the group consisting of replicase activity, RNA polymerase activity, reverse transcriptase activity, helicase activity, ATP hydrolysis activity, GTP hydrolysis activity, primase activity, nucleic acid binding activity, and nicking activity, and wherein said modified AL1 protein comprises a substitution selected from the group consisting of -Ala-Leu-Glu- for -Gly2 and -Thr-Leu-Glu- for -Xaa2-Xaa3-Xaa4-Gly2- in an amino acid domain having the sequence -Gly1-Xaa1-Xaa2-Xaa3-Xaa4-Gly2-Lys- (SEQ ID NO.1).

2. A DNA molecule of claim 1 in which the AL1 protein is from tomato golden mosaic virus (TGMV).

3. A DNA molecule which comprises operatively linked in sequence in the 5' to 3' direction:

(a) a promoter region which functions in plant cells to cause the production of an RNA sequence;

(b) a structural gene encoding a modified form of an AL1 protein normally required fro the replication of a gemini virus of tomato wherein the unmodified AL1 protein is a protein which has an activity associated with it of the type selected from the group consisting of replicase activity, RNA polymerase activity, reverse transcriptase activity, helicase activity, ATP hydrolysis activity, GTP hydrolysis activity, primase activity, nucleic acid binding activity, and nicking activity, and wherein said modified AL1 protein comprises a substitution selected from the group consisting of -Ala-Leu-Glu- for -Gly2 and -Thr-Leu-Glu for -Xaa2-Xaa3-Xaa4-Gly2- in an amino acid domain having the sequence -Gly1-Xaa1-Xaa2-Xaa3-Xaa4-Gly2-Lys-(SEQ ID NO.1); and (c) a non translated DNA sequence which functions in plant cells to cause the termination of transcription and the addition of polyadenylated ribonucleotides to the 3' end of the transcribed MRNA sequence.

4. A DNA molecule of claim 3 in which said promoter region is selected from the group consisting of the FMV35S promoter regions and the CaMV35S promoter regions.

5. A DNA molecule of claim 4 in which said 3' non-translated region is selected from a gene of the group consisting of the nopaline synthase genes, the soybean 7S storage protein genes, the pea small subunit of the ribulose 1,5-bisphosphate carboxylase-oxygenase (ssRUBISCO) genes, and E9 gene.

6. A DNA molecule of claim 5 in which the AL1 protein is from tomato golden mosaic virus (TGMV).

7. A method for providing resistance to infection by gemini viruses of tomato in a susceptible plant which comprises:

(a) transforming susceptible plant cells with a DNA molecule which comprises operatively linked in sequence in the 5' to 3' direction:

(i) a promoter region which functions in plant cells to cause the production of an RNA sequence;

(ii) a structural gene encoding a modified form of an AL1 protein normally required for the replication of a gemini virus of tomato wherein the unmodified AL1 protein is a protein which has an activity associated with its of the type selected from the group consisting of replicase activity, RNA polymerase activity, reverse transcriptase activity, helicase activity, ATP hydrolysis activity, GTP hydrolysis activity, primase activity, nucleic acid binding activity, and nicking activity, and wherein said modified AL1 protein comprises a substitution selected from the group consisting of -Ala-Leu-Glu- for Gly2 and -Thr-Leu-Glu for -Xaa2-Xaa3-Xaa4-Gly2- in an amino acid domain having the sequence -Gly1-Xaa1-Xaa2-Xaa3-Xaa4-Gly2-Lys- (SEQ ID NO.1); and (iii) a non translated DNA sequence which functions in plant cells to cause the termination of transcription and the addition of polyadenylated ribonucleotides to the 3' end of the transcribed mRNA sequence;

(b) selecting said plant cells which have been transformed;

(c) regenerating said plant cells to provide a differentiated plant; and (d) selecting a transformed plant which expresses said structural gene at a level sufficient to render the plant resistant to infection by the gemini viruses of tomato from which the AL1 protein gene was derived.

8. A method of claim 7 in which said plant is tomato.

9. A method of claim 7 in which said plant is tobacco.

10. A method of claim 9in which the AL1 protein is from tomato golden mosaic virus (TGMV).

11. A virus-resistant transformed plant normally susceptible to infection by a gemini virus of tomato having inserted into its genome a DNA molecule which comprises operatively linked in sequence in the 5' to 3' direction:

(a) a promoter region which functions in plant cells to cause the production of an RNA sequence;

(b) a structural gene encoding a modified from of an AL1 protein normally required fro the replication of a gemini virus of tomato wherein the unmodified AL1 protein is a protein which as an activity associated with it of the type selected from the group consisting of replicase activity, RNA polymerase activity, reverse transcriptase activity, helicase activity, ATP hydrolysis activity, GTP hydrolysis activity, primase activity, nucleic acid binding activity, and nicking activity, and wherein said modified AL1 protein comprises a substitution selected from the group consisting of -Ala-Leu-Glu- for -Gly2 and -Thr-Leu-Glu- for -Xaa2-Xaa3-Xaa4-Gly2- in an amino acid domain having the sequence -Gly1-Xaa1-Xaa2-Xaa3-Xaa4-Gly2-Lys-(SEQ ID NO.1); and (c) a non-translated DNA sequence which functions in plant cells to cause the termination of transcription and the addition of polyadenylated ribonucleotides to the 3' end of the transcribed mRNA sequence.

12. A plant of claim 11 in which said DNA molecule contains a promoter region is selected from the group consisting of the FMV35S promoter regions and the CaMV35S promoter regions.

13. A plant of claim 12 in which said plant is tomato.

14. A plant of claim 12 in which said plant is tobacco.

15. A plant of claim 14 in which the AL1 protein is from tomato golden mosaic virus (TGMV).

* * * * *

UNITED STATES PATENT AND TRADEMARK OFFICE
CERTIFICATE OF CORRECTION

PATENT NO. : 5,850,023
DATED : December 15, 1998
INVENTOR(S) : James Scott Emer/Daniel Nathans/Stephen Gary Rogers It is certified that error appears in the above-identified patent and that said Letters Patent is hereby corrected as shown below:

In claim 3(b), column 31, line 36, before "the" and after "required," delete "fro" and insert therefor --for--.

In claim 3(c), column 31, line 53, before "sequence" and after "transcribed," delete "MRNA" and insert therefor --mRNA--.

In claim 7(ii), column 32, line 24, before "of" and after "with," delete "its" and insert therefor --it--.

In claim 11(b), column 32, line 59, before "of "and after "modified," delete "from" and insert therefor --form--.

In claim 11(b), column 32, line 60, before "the" and after "required," delete "fro" and insert therefor --for--.

In claim 11(b), column 32, line 62, before "an" and after "which," delete "as" and insert therefor --has--.

Signed and Sealed this

Twenty-ninth Day of June, 1999

Attest:

Q. TODD DICKINSON

*Attesting Officer*      Acting Commissioner of Patents and Trademarks